United States Patent
Shanjani et al.

(10) Patent No.: US 11,576,766 B2
(45) Date of Patent: Feb. 14, 2023

(54) BIOSENSOR PERFORMANCE INDICATOR FOR INTRAORAL APPLIANCES

(71) Applicant: Align Technology, Inc., San Jose, CA (US)

(72) Inventors: Yaser Shanjani, Milpitas, CA (US); Bruce Cam, San Jose, CA (US); John Y. Morton, San Jose, CA (US); Jun Sato, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 272 days.

(21) Appl. No.: 16/814,868

(22) Filed: Mar. 10, 2020

(65) Prior Publication Data

US 2020/0214817 A1 Jul. 9, 2020

Related U.S. Application Data

(63) Continuation of application No. 16/019,037, filed on Jun. 26, 2018.
(Continued)

(51) Int. Cl.
*A61C 19/04* (2006.01)
*A61K 49/00* (2006.01)
(Continued)

(52) U.S. Cl.
CPC .............. *A61C 19/04* (2013.01); *A61B 5/1111* (2013.01); *A61B 5/4542* (2013.01);
(Continued)

(58) Field of Classification Search
CPC ......... A61C 19/04; A61C 7/08; A61B 5/1111; A61B 5/4542; A61B 5/4547;
(Continued)

(56) References Cited

U.S. PATENT DOCUMENTS 3,092,907 A 6/1963 Traiger
3,797,115 A 3/1974 Cohen et al.
(Continued)

FOREIGN PATENT DOCUMENTS

DE 202012011899 U1 1/2013
JP 2007537824 A 12/2007
(Continued)

OTHER PUBLICATIONS

Florez-Moreno et al, "Time-related changes in salivary levels of the osteotropic factors sRANKL and OPG through orthodontic tooth movement", Jan. 2013, American Journal of Orthodontics and Dentafacial Orthopedic, vol. 143, pp. 92-100 (Year: 2013).*
(Continued)

*Primary Examiner* — Jacqueline T Johanas
*Assistant Examiner* — Shannel Nicole Belk
(74) *Attorney, Agent, or Firm* — Shay Glenn LLP

(57) ABSTRACT

Methods and apparatuses for monitoring either or both the performance of an orthodontic appliance for repositioning a patient's teeth and/or the user compliance in wearing the appliance using a biosensor. The apparatuses described herein may include one or more sensors, including biosensors, electrical sensors, or both, configured to generate sensor data related to user compliance and/or repositioning of the patient's teeth by an orthodontic appliance.

19 Claims, 12 Drawing Sheets

Related U.S. Application Data

(60) Provisional application No. 62/525,082, filed on Jun. 26, 2017.

(51) Int. Cl.
*A61B 5/11* (2006.01)
*A61C 7/08* (2006.01)
*A61B 5/00* (2006.01)
*A61B 5/145* (2006.01)

(52) U.S. Cl.
CPC .......... *A61B 5/4547* (2013.01); *A61B 5/4833* (2013.01); *A61B 5/682* (2013.01); *A61C 7/08* (2013.01); *A61K 49/0004* (2013.01); *A61B 5/14507* (2013.01); *A61B 5/14546* (2013.01)

(58) Field of Classification Search
CPC .............. A61B 5/4833; A61B 5/14507; A61B 5/1456; A61B 5/4277
See application file for complete search history.

(56) References Cited

U.S. PATENT DOCUMENTS

| | | |
|---|---|---|
| 4,094,068 A | 6/1978 | Schinhammer |
| 4,129,946 A | 12/1978 | Kennedy |
| 4,134,208 A | 1/1979 | Pearlman |
| 4,179,812 A | 12/1979 | White |
| 4,204,325 A | 5/1980 | Kaelble |
| 4,368,040 A | 1/1983 | Weissman |
| 4,505,672 A | 3/1985 | Kurz |
| 4,523,908 A | 6/1985 | Drisaldi et al. |
| 4,971,557 A | 11/1990 | Martin |
| 5,615,183 A | 3/1997 | Ishii |
| 5,636,736 A | 6/1997 | Jacobs et al. |
| 5,816,199 A | 10/1998 | Khizh et al. |
| 5,820,368 A | 10/1998 | Wolk |
| 5,975,893 A | 11/1999 | Chishti et al. |
| 6,102,701 A | 8/2000 | Engeron |
| 6,120,287 A | 9/2000 | Chen |
| 6,183,248 B1 | 2/2001 | Chishti et al. |
| 6,210,162 B1 | 4/2001 | Chishti et al. |
| 6,213,767 B1 | 4/2001 | Dixon et al. |
| 6,234,990 B1 | 5/2001 | Rowe et al. |
| 6,309,215 B1 | 10/2001 | Phan et al. |
| 6,386,864 B1 | 5/2002 | Kuo |
| 6,450,807 B1 | 9/2002 | Chishti et al. |
| 6,454,565 B2 | 9/2002 | Phan et al. |
| 6,471,511 B1 | 10/2002 | Chishti et al. |
| 6,524,101 B1 | 2/2003 | Phan et al. |
| 6,572,372 B1 | 6/2003 | Phan et al. |
| 6,607,382 B1 | 8/2003 | Kuo et al. |
| 6,705,863 B2 | 3/2004 | Phan et al. |
| 6,736,638 B1 | 5/2004 | Sachdeva et al. |
| 6,769,913 B2 | 8/2004 | Hurson |
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,843,370 B2 | 1/2005 | Tuneberg |
| 6,947,038 B1 | 9/2005 | Anh et al. |
| 6,983,752 B2 | 1/2006 | Garabadian |
| 6,988,893 B2 | 1/2006 | Haywood |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,229,282 B2 | 6/2007 | Andreiko et al. |
| 7,294,141 B2 | 11/2007 | Bergersen |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,637,740 B2 | 12/2009 | Knopp |
| 7,641,473 B2 | 1/2010 | Sporbert et al. |
| 7,658,610 B2 | 2/2010 | Knopp |
| 7,766,658 B2 | 8/2010 | Tricca et al. |
| 7,771,195 B2 | 8/2010 | Knopp et al. |
| 7,841,464 B2 | 11/2010 | Cinader, Jr. et al. |
| 7,854,609 B2 | 12/2010 | Chen et al. |
| 7,869,983 B2 | 1/2011 | Raby et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,947,508 B2 | 5/2011 | Tricca et al. |
| 8,029,277 B2 | 10/2011 | Imgrund et al. |
| 8,075,306 B2 | 12/2011 | Kitching et al. |
| 8,136,529 B2 | 3/2012 | Kelly |
| 8,152,518 B2 | 4/2012 | Kuo |
| 8,172,569 B2 | 5/2012 | Matty et al. |
| 8,197,252 B1 | 6/2012 | Harrison, III |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,401,826 B2 | 3/2013 | Cheng et al. |
| 8,419,428 B2 | 4/2013 | Lawrence |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,753,114 B2 | 6/2014 | Vuillemot |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,220,580 B2 | 12/2015 | Borovinskih et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |

(56) References Cited

U.S. PATENT DOCUMENTS

| | | |
|---|---|---|
| 10,912,629 B2 | 2/2021 | Tanugula et al. |
| 10,959,810 B2 | 3/2021 | Li et al. |
| 10,993,783 B2 | 5/2021 | Wu et al. |
| 2002/0192617 A1 | 12/2002 | Phan et al. |
| 2003/0059736 A1 | 3/2003 | Lai et al. |
| 2003/0060532 A1 | 3/2003 | Subelka et al. |
| 2003/0101079 A1 | 5/2003 | Mclaughlin |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0040551 A1 | 2/2005 | Biegler et al. |
| 2005/0042577 A1 | 2/2005 | Kvitrud et al. |
| 2005/0113317 A1 | 5/2005 | Robinson et al. |
| 2005/0186524 A1 | 8/2005 | Abolfathi et al. |
| 2005/0244768 A1 | 11/2005 | Taub et al. |
| 2005/0244791 A1 | 11/2005 | Davis et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0223023 A1 | 10/2006 | Lai et al. |
| 2006/0234179 A1 | 10/2006 | Wen et al. |
| 2007/0065768 A1 | 3/2007 | Nadav |
| 2007/0218422 A1 | 9/2007 | Ehrenfeld |
| 2007/0263226 A1 | 11/2007 | Kurtz et al. |
| 2008/0118882 A1 | 5/2008 | Su |
| 2008/0119698 A1* | 5/2008 | Tricca ............... A61B 5/4839 600/309 |
| 2008/0160473 A1 | 7/2008 | Li et al. |
| 2008/0268400 A1 | 10/2008 | Moss et al. |
| 2008/0286716 A1 | 11/2008 | Sherwood |
| 2008/0286717 A1 | 11/2008 | Sherwood |
| 2008/0306724 A1 | 12/2008 | Kitching et al. |
| 2009/0117507 A1* | 5/2009 | Abolfathi ............... A61C 7/00 433/80 |
| 2009/0170050 A1 | 7/2009 | Marcus |
| 2009/0280450 A1 | 11/2009 | Kuo |
| 2010/0015565 A1 | 1/2010 | Carrillo et al. |
| 2010/0028825 A1 | 2/2010 | Lemchen |
| 2010/0055635 A1 | 3/2010 | Kakavand |
| 2010/0062394 A1 | 3/2010 | Jones et al. |
| 2010/0129763 A1 | 5/2010 | Kuo |
| 2010/0196837 A1 | 8/2010 | Farrell |
| 2010/0217130 A1 | 8/2010 | Weinlaender |
| 2011/0136090 A1 | 6/2011 | Kazemi |
| 2011/0207072 A1 | 8/2011 | Schiemann |
| 2011/0212420 A1 | 9/2011 | Vuillemot |
| 2011/0269092 A1 | 11/2011 | Kuo et al. |
| 2012/0028210 A1 | 2/2012 | Hegyi et al. |
| 2014/0067334 A1 | 3/2014 | Kuo |
| 2014/0178829 A1 | 6/2014 | Kim |
| 2014/0342301 A1 | 11/2014 | Fleer et al. |
| 2015/0216716 A1 | 8/2015 | Anitua |
| 2015/0265376 A1 | 9/2015 | Kopelman |
| 2015/0366637 A1 | 12/2015 | Kopelman et al. |
| 2015/0366638 A1 | 12/2015 | Kopelman et al. |
| 2016/0193014 A1 | 7/2016 | Morton et al. |
| 2016/0242870 A1 | 8/2016 | Matov et al. |
| 2016/0242871 A1* | 8/2016 | Morton ................ A61C 7/002 |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007365 A1 | 1/2017 | Kopelman et al. |
| 2017/0007366 A1 | 1/2017 | Kopelman et al. |
| 2017/0007386 A1 | 1/2017 | Mason et al. |
| 2017/0115236 A1 | 4/2017 | Renlund et al. |
| 2017/0122846 A1 | 5/2017 | Holmes et al. |
| 2017/0135792 A1 | 5/2017 | Webber |
| 2017/0135793 A1 | 5/2017 | Webber et al. |
| 2017/0165032 A1 | 6/2017 | Webber et al. |
| 2017/0319296 A1 | 11/2017 | Webber et al. |
| 2017/0347956 A1* | 12/2017 | Zegarelli ............ A61B 5/0833 |
| 2018/0078334 A1 | 3/2018 | Lotan et al. |
| 2018/0085059 A1* | 3/2018 | Lee ................. A61B 5/682 |
| 2018/0153648 A1 | 6/2018 | Shanjani et al. |
| 2018/0153733 A1 | 6/2018 | Kuo |
| 2018/0168776 A1 | 6/2018 | Webber |
| 2018/0228359 A1 | 8/2018 | Meyer et al. |
| 2018/0280118 A1 | 10/2018 | Cramer |
| 2018/0353264 A1 | 12/2018 | Riley et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0029775 A1 | 1/2019 | Morton et al. |
| 2019/0046297 A1 | 2/2019 | Kopelman et al. |
| 2019/0069975 A1 | 3/2019 | Cam et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0231477 A1 | 8/2019 | Shanjani et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0338067 A1 | 11/2019 | Liska et al. |
| 2019/0343606 A1 | 11/2019 | Wu et al. |
| 2020/0000553 A1 | 1/2020 | Makarenkova et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0100871 A1 | 4/2020 | Wang et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |

FOREIGN PATENT DOCUMENTS

| | | | |
|---|---|---|---|
| KR | 20070108019 A | 11/2007 | |
| TW | 480166 B | 3/2002 | |
| WO | 0185047 A2 | 11/2001 | |
| WO | 2013058879 A2 | 4/2013 | |
| WO | 2014143911 A1 | 9/2014 | |
| WO | WO-2016142414 A1 * | 9/2016 | ............ A61C 19/04 |

OTHER PUBLICATIONS

D'Apuzzo et al, "Biomarkers of Periodontal Tissue Remodeling during Orthodontic Tooth Movement in Mice and Men: Overview and Clinical Relevance", Apr. 23, 2013, The Scientific World Journal (Year: 2013).*

"Identify." Merriam-Webster.com Dictionary, Merriam-Webster, https://www.merriam-webster.com/dictionary/identify. Accessed Apr. 3, 2022. (Year: 2022).*

Alves R.C., et al., "New Trends in Food Allergens Detection: Toward Biosensing Strategies", Critical Reviews in Food Science and Nutrition, Mar. 2015, 18 pages.

Ellias M.F., et al., "Proteomic Analysis of Saliva Identifies Potential Biomarkers for Orthodontic Tooth Movement", The Scientific World Journal, 2012, vol. 2012, Article ID: 647240, 7 pages.

Florez-Moreno, Time-related changes in salivary levels of the osteotropic factors sRANKL and OPG through orthodontic tooth movement, American Journal of Orthodontics and Dentofacial Orthopedics, Jan. 2013, 143 (1), pp. 92-100.

Bernabe et al., Are the lower incisors the best predictors for the unerupted canine and premolars sums? An analysis of peruvian sample, The Angle Orthodontist, Mar. 2005, 75(2), pp. 202-207.

Collins English Dictionary, Teeth (definition), 9 pages, retrieved from the internet (https://www.collinsdictionary.com/us/dictionary/english/teeth) on May 13, 2019.

Dental Monitoring, "BASICS: How to put your Cheek Retractor? (Dental Monitoring Tutorial)", https://www.youtube.com/watch?v=6K1HXw4Kq3c, May 27, 2016.

(56) References Cited

OTHER PUBLICATIONS

Dental Monitoring, Dental monitoring tutorial, 1 page (Screenshot), retrieved from the internet (https:www.youtube.com/watch?v=Dbe3ud0f9_c), Mar. 18, 2015.

Dictionary.com, Plural (definition), 6 pages, retrieved from the internet (https://www.dictionary.com/browse/plural#) on May 13, 2019.

Dictionary.com, Quadrant (definition), 6 pages, retrieved from the internet ( https://www.dictionary.com/browse/quadrant?s=t) on May 13, 2019.

Eclinger Selfie, Change your smile, 1 page (screenshot), retrieved from the internet https://play.google.com/store/apps/details?id=parkelict.ecligner), on Feb. 13, 2018.

Martinelli et al., Prediction of lower permanent canine and premolars width by correlation methods, The Angle Orthodontist, 75(5), pp. 805-808, Sep. 2005.

Nourallah et al., New regression equations for predicting the size of unerupted canines and premolars in a contemporary population, The Angle Orthodontist, 72(3), pp. 216-221, Jun. 2002.

Paredes et al., A new, accurate and fast digital method to predict unerupted tooth size, The Angle Orthodontist, 76 (1), pp. 14-19, Jan. 2006.

* cited by examiner

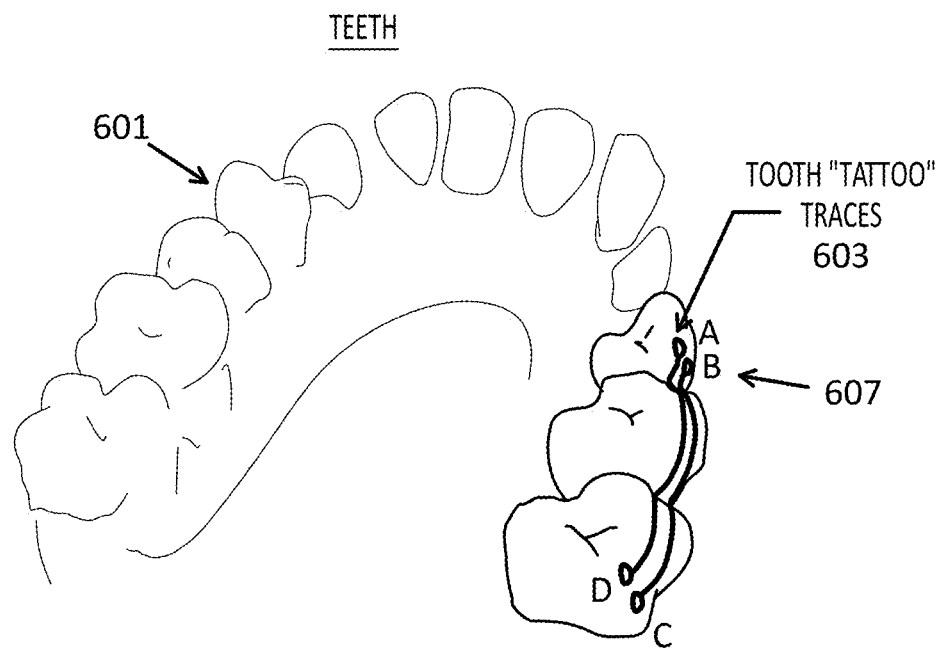
FIG. 6A
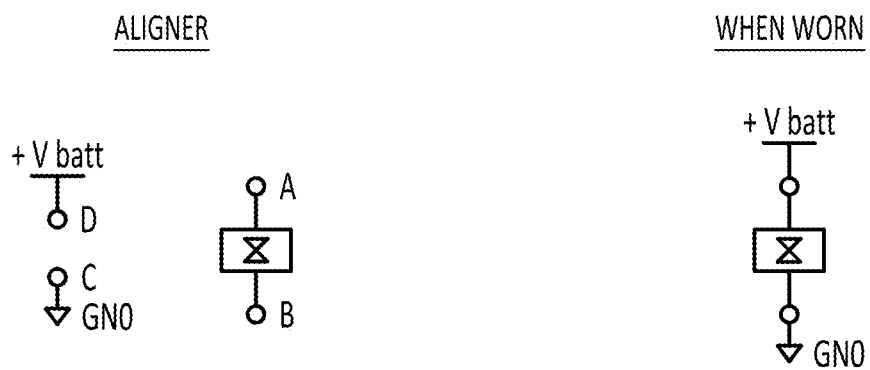
FIG. 6B
FIG. 6C

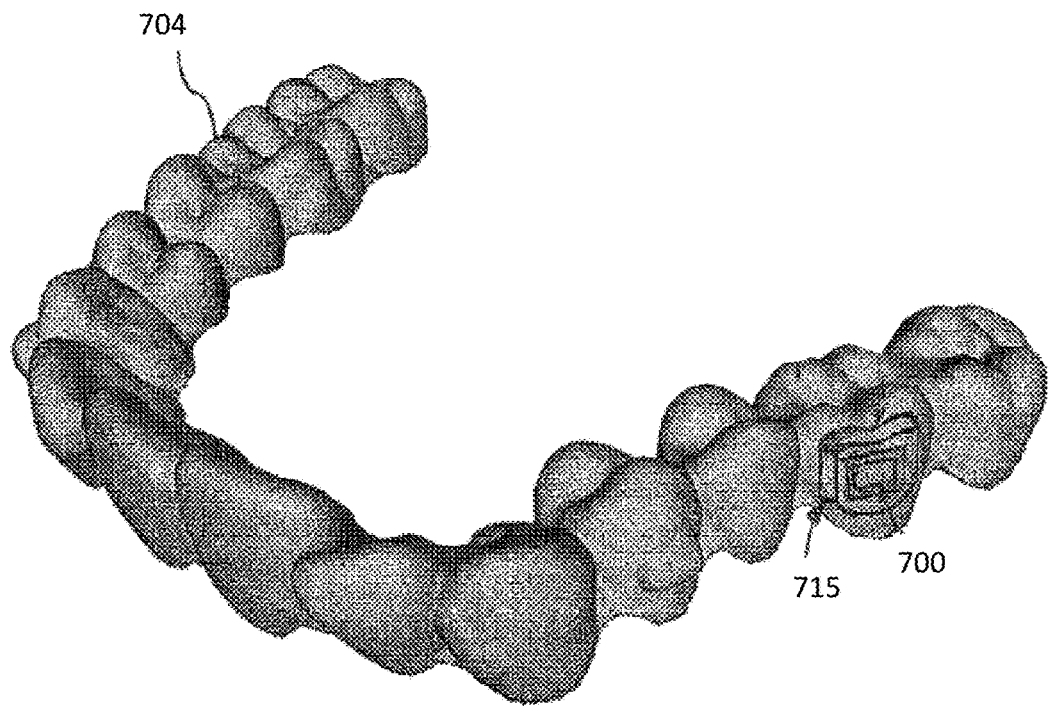
FIG. 7A
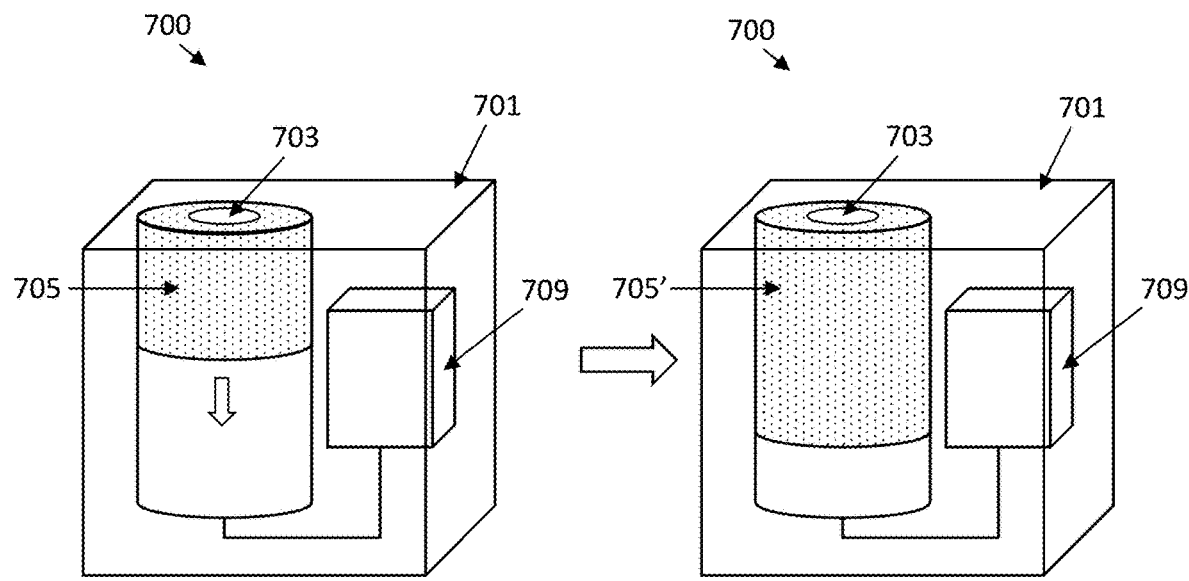
FIG. 7B            FIG. 7C

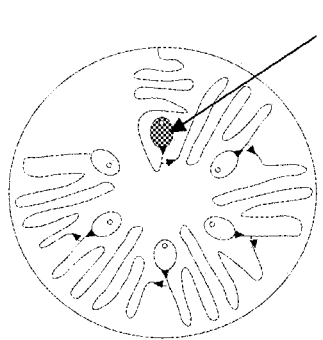
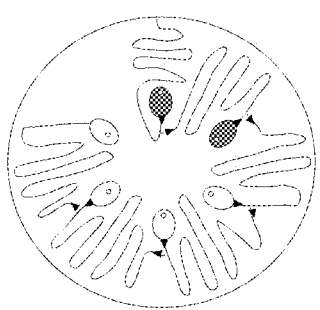
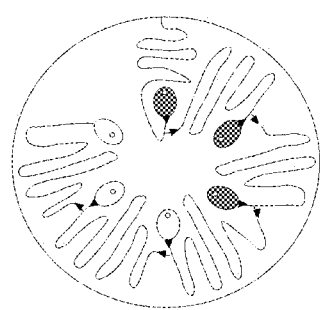
FIG. 10C    FIG. 10D    FIG. 10E
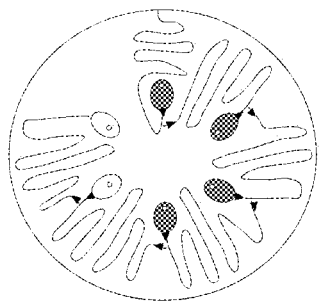
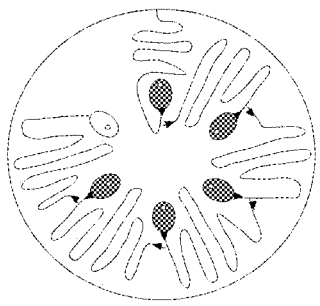
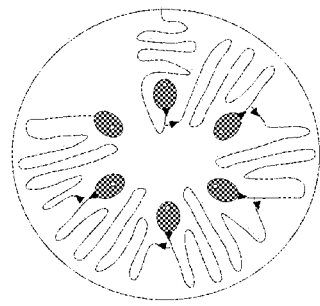
FIG. 10F    FIG. 10G    FIG. 10H
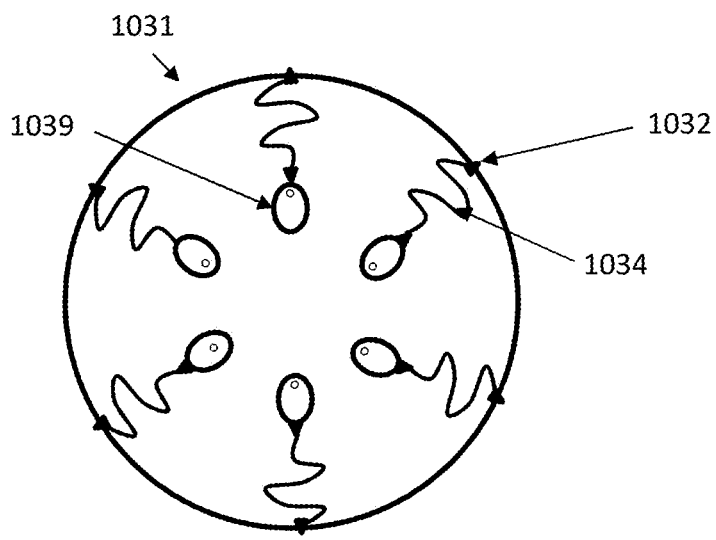
FIG. 11

BIOSENSOR PERFORMANCE INDICATOR FOR INTRAORAL APPLIANCES

CROSS REFERENCE TO RELATED APPLICATIONS

This patent application is a continuation of U.S. patent application Ser. No. 16/019,037, filed on Jun. 26, 2018, titled "BIOSENSOR PERFORMANCE INDICATOR FOR INTRAORAL APPLIANCES," which claims priority to U.S. Provisional Patent Application No. 62/525,082, filed Jun. 26, 2017, titled "BIOSENSOR PERFORMANCE INDICATOR FOR INTRAORAL APPLIANCES," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Orthodontic appliances, including dental appliances, including shell aligners, with one or more sensors for monitoring use and/or progress of the appliance.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan.

During orthodontic treatment with patient-removable appliances, the practitioner may rely on the patient to comply with the prescribed appliance usage. In some instances, a patient may not wear the orthodontic appliance as prescribed by the practitioner. Extended removal of the appliance, for any reason beyond what is recommended, may interrupt the treatment plan and lengthen the overall period of treatment.

In some instances, the forces that are actually applied to a patient's teeth by an orthodontic appliance may differ from the intended forces for treating the teeth. Discrepancies between the planned and achieved repositioning forces may result in incomplete or undesirable tooth movements and deviations from the prescribed treatment plan. Accordingly, improved approaches for monitoring orthodontic appliance performance, treatment progress, and patient compliance are needed.

SUMMARY OF THE DISCLOSURE

In general, described herein are methods and apparatuses for detecting one or more biomarkers from within a subject's oral cavity. The apparatuses (including devices and systems) described herein may include any oral appliance, including (but not limited to) aligners, palatal expanders, retainers, and the like.

For example, described herein are methods and apparatuses (including systems and devices) for monitoring one or more of: the performance of an orthodontic appliance for repositioning a patient's teeth, the patient's physiological condition and/or the user compliance in wearing the appliance. The apparatuses described herein may include one or more sensors, including bio sensors, electrical sensors, or both, configured to generate sensor data related to user compliance and/or repositioning of the patient's teeth by an orthodontic appliance. For example, the data can be indicative of patient wearing compliance, the amount of tooth movement achieved, the amount of force and/or pressure actually applied to the teeth by the appliance, bone remodeling processes and stages, tissue health, bacterial activity in the oral cavity, or any combination thereof. Advantageously, the embodiments described herein provide high value data that allows the practitioner to quantitatively assess whether the orthodontic appliance is repositioning the patient's teeth as planned. The data can be used as feedback to adjust the patient's treatment plan, also known as "adaptive closed-loop treatment," and can also inform the design and planning of future appliance based orthodontic procedures. Based on such data, a treatment plan can be adaptively modified. For instance, to estimate whether and when the patient is ready for next stage Aligner.

This methods and apparatuses described herein may be used for monitoring and analysis of bioagents in the intraoral cavity while an intra-oral appliance (e.g., aligner, palatal expander, etc.) is in use. These apparatuses and methods may collect information (data), including data about tooth movement phases, via analysis of biomarkers in saliva or gingival crevicular fluid (GCF).

Also described herein are apparatuses for monitoring patient compliance and/or performance of an orthodontic appliance for repositioning a patient's teeth. These apparatuses may include an orthodontic appliance, such as an aligner comprising one or more teeth-receiving cavities shaped to reposition the patient's teeth from an initial arrangement towards a target arrangement and one or more sensors, including biosensors, configured to generate sensor data. The sensor data may be related to one or more biomarkers from saliva and/or GCF. The apparatus may also comprise a processor configured to process the sensor data, to evaluate the performance of the orthodontic appliance in effecting the repositioning of the patient's teeth, patient health including oral health, and/or patient compliance.

Thus, an orthodontic appliance as described herein may include one or more biosensors configured to obtain data indicative of a biomarker in the patient's saliva, GCF, tissue or tissue (including tooth) surface, and one or more processors operably coupled to the biosensor(s) and configured to process the biosensor data so as to generate patient compliance data (e.g., enabling electronic monitoring of patient compliance with a prescribed course of orthodontic treatment), patient treatment monitoring data, and/or patient health (e.g., oral health) data. Advantageously, these apparatuses and methods may increase improve treatment efficacy and may provide patient data useful to the practitioner for designing and monitoring orthodontic treatments.

Thus, described herein are devices for repositioning a patient's teeth and monitoring a biomarker indicative of performance of the device and/or patient compliance in wearing the device. Any of these devices may include: an orthodontic appliance comprising one or more (e.g., a plurality of) teeth-receiving cavities shaped to reposition the patient's teeth from an initial arrangement towards a target arrangement; a biosensor comprising a bioreceptor material configured to specifically interact with the biomarker and a biotransducer material configured to transduced interaction of the bioreceptor with the biomarker into an electrical signal; and a processor in electrical communication with the biosensor and configured to process the electrical signal into sensor data to evaluate one or more of: the performance of the orthodontic appliance in effecting the repositioning of the patient's teeth and patient compliance.

In general, the bioreceptor may comprise a protein that selectively binds to the biomarker. For example, the bioreceptor may include a primary and/or a secondary protein, such or a portion of protein, such as an antibody, antibody fragment, or the like, including antibody-based molecules, and/or enzymes. In general, any molecule that recognizes a target molecule with specificity may be used. For example, the bioreceptor may be an enzyme that selectively acts on the biomarker.

Any biomarker may be targeted, particularly but not exclusively a biomarker present in saliva. Alternatively, the biomarker may be a biomarker in the blood, gingiva, or teeth. In some cases, the biomarker may be a biomechanical property, such as heart rate, blood pressure, or the like. Biomarkers that may be present in saliva may include one or more of: Calgranulin-B, Serum albumin precursor, Immunoglobulin J chain, Ig alpha-1 chain C region, Cysteine-rich secretory protein 3 precursor (CRISP-3), Hemoglobin subunit beta, Stratifin, and soluble RANK Ligand (sRANKL). The biomarker may be present in gingival crevicular fluid (GCF). For example, the biomarker may be one or more of: prostaglandin E2, Substance P, epidermal growth factor, transforming growth factor, Receptor activator of nuclear factor kappa-B ligand (RANKL), Granulocyet macrophage colony stimulation factor, $\alpha 2$ microglobulin, Interleukin $1\beta$, Myeloperoxidase, hyaluronic acid and Chondroitin sulfate.

Further, any appropriate biosensor may be used, including electrodes. For example, the biosensor may comprise an electrode made nanowires and/or nanoparticles. Carbon nanotubes, graphene, noble metal-based nanoparticles and the like can be used to form all or portion of the biosensor(s) herein, for example, by forming a conductive trace. These materials may be patterned, including forming onto an orthodontic device as a flexible trace, e.g., using a printed or otherwise applied conductive ink. The conductive ink may include a material (such as an elastomeric binder) to increase flexibility. For example, the biosensor may comprise a conductive ink and an elastomeric binder such as one or more of: silicone, fluorine rubber, polyurethane and isoprene block co-polymers. Flexible electrodes/conductive traces may be used as part of the biosensor and as connections between the biosensor and any other components, including the processor. Examples of conductive ink include: activate carbon knitted carbon fibers (with a binder such as, e.g., polytetrafluoroethylene as a), RhO2/SWCNT (with a binder such as, e.g., sodium dodecyl sulfate), graphene (with a binder such as, e.g., ethyl cellulose), Ketjenblack porous carbon (with a binder such as, e.g., a styrene-butadiene rubber), PEG coated silver flakes (with a binder such as, e.g., a polyurethane), Ag/AgCl ink and/or multi-walled carbon nanotube (MWCNT) and silver (Ag) nanoparticles (with a binder such as, e.g., a polyurethane), silver flakes or silver particles (with a binder such as, e.g., a binder such as, e.g., copolymer fluoroelastomer of vinylidene-fluoride/Hexfluoropropylene Zonyl-FS 300 fluorosurfactant and/or hexyl acetate capsules with organic solvent (hexyl acetate) acrylic).

The bio sensor may include a conductive substrate to which the biotransducer is attached and an insulating layer. In general, any of these devices may include a reference electrode comprising the biotransducer material but not a bioreceptor material. Further, any of these devices may include a plurality of biosensors operably coupled to different portions of the orthodontic appliance.

Any of these devices may include a second (or more) sensor operatively coupled to the orthodontic appliance, wherein the additional sensor(s) comprises one or more of: a force or pressure sensor, a temperature sensor, or a movement sensor.

In general, the biosensor may be integrated with the orthodontic appliance, coupled to a tooth, or a combination thereof. Any of these devices may include a communication module configured to transmit the sensor data to a remote device.

Any of the apparatuses described herein may include one or more microneedles, including arrays of microneedles. See, e.g., PCT/US2012/053544 (herein incorporated by reference in its entirety) for examples of microneedles that may be used in any of the apparatuses described herein. In general, these apparatuses (and methods of using them) may include a mechanism such a microneedle for drawing and detecting any of the analytes described herein. For example, an array of hollow probes (e.g., tubes, needles, etc.) can extract biomaterial transdermally. In some variations the probes may include amperometric, voltamemertric, or potentiometric sensors within the probe to measure analytes in the sample.

Also described herein are methods of monitoring an orthodontic device in a subject's oral cavity. These methods may be used to modify a dental treatment plan (e.g., an orthodontic treatment plan). Also, in general, any of these methods may be used for monitoring oral health, generally, regardless of the performance of the aligner. Thus, any of these methods may be configured as methods of monitoring a subject's health (or oral health) using any of the devices and methods described herein.

For example, a method of monitoring an orthodontic device in a subject's oral cavity may include: inserting an orthodontic appliance comprising one or more teeth-receiving cavities shaped to reposition the patient's teeth from an initial arrangement towards a target arrangement onto the patient's teeth; detecting a biomarker within the subject's saliva or gingival crevicular fluid using a bio sensor configured to specifically interact with the biomarker coupled to the orthodontic appliance; and processing signals from the biosensor to evaluate one or more of: the performance of the orthodontic appliance in effecting the repositioning of the patient's teeth and patient compliance.

Detecting the biomarker may include detecting the biomarker within the subject's saliva. For example, detecting the biomarker may include detecting at least one of: Calgranulin-B, Serum albumin precursor, Immunoglobulin J chain, Ig alpha-1 chain C region, Cysteine-rich secretory protein 3 precursor (CRISP-3), Hemoglobin subunit beta, Stratifin, and soluble RANK Ligand (sRANKL). Detecting the biomarker may comprises detecting the biomarker within the subject's gingival crevicular fluid; for example, detecting the biomarker may comprise detecting at least one of: prostaglandin E2, Substance P, epidermal growth factor, transforming growth factor, Receptor activator of nuclear factor kappa-B ligand (RANKL), Granulocyet macrophage colony stimulation factor, $\alpha 2$ microglobulin, Interleukin $1\beta$, Myeloperoxidase, hyaluronic acid and Chondroitin sulfate. Detecting the biomarker may comprise detecting an interaction between the biomarker and a bioreceptor of the biomarker that is transduced by a biotransducer of the biosensor into an electrical signal.

In general, processing signals from the biosensor may include wirelessly transmitting the signals, and/or transmitting them via a wired connection.

As mentioned, any of these methods may be configured to modify a patient therapy based on the output of the sensing, including modifying a treatment plan (e.g., orthodontic treatment plan). For example, processing the signals may comprise modifying an orthodontic treatment plan for the patient based on the signals. Alternatively, any of these methods may include modifying the treatment plan. Modifying the orthodontic treatment plan may comprise generating a second orthodontic appliance comprising one or more teeth-receiving cavities shaped to reposition the patient's teeth from a current arrangement towards a second target arrangement. Modifying the orthodontic treatment plan may comprise removing the orthodontic appliance.

Also described herein are systems in which the aligner include an open circuit that is closed when the patient wears the aligner on their teeth. For example, described herein are systems for repositioning a patient's teeth and monitoring a biomarker indicative of performance of an orthodontic appliance and/or patient compliance in wearing the appliance, the system comprising: the orthodontic appliance comprising one or more (e.g., a plurality of) teeth-receiving cavities shaped to reposition the patient's teeth from an initial arrangement towards a target arrangement; a first electrical contact within the teeth-receiving cavity of the orthodontic appliance; a second electrical contact within the teeth-receiving cavity of the orthodontic appliance; an electrical circuit coupled to the first electrical contact and the second electrical contact, wherein the electrical circuit is open until the orthodontic appliance is worn on the patient's teeth so that an electrical trace on the patient's tooth or teeth couples to both first electrical contact and the second electrical contact to close the electrical circuit; and a processor in electrical communication with the electrical circuit and configured to generate a signal when the electrical circuit between the first electrical contact and the second electrical contact is closed.

Any of these systems may include an electrically conductive trace configured to be mounted on the patient's teeth, the electrically conductive trace having a first node and a second node, wherein the first node is configured to contact the first electrical contact and the second node is configured to contact the second electrical contact.

These systems may also include one or more sensors coupled to the electrical circuit, wherein the sensor is configured to operate when the electrical circuit is closed.

These systems may include a power source on the orthodontic appliance. The power source may be a battery or the like, particularly a rechargeable battery. In any of the devices and systems described herein, the power source may include a biofuel cell sensor that is powered using metabolites in saliva as fuel as well as analytes.

Any of these systems and devices may include a processor, and the processor may be configured to wirelessly transmit the signal. The processor may comprise a data logger to record the signals. The processor may be configured to periodically transmit the signal while the electrical circuit is closed.

Also described herein are methods of determining patient compliance in wearing an orthodontic appliance that comprises one or more teeth-receiving cavities shaped to reposition the patient's teeth from an initial arrangement towards a target arrangement. For example, the method may include: closing an electrical circuit on the orthodontic appliance by placing the orthodontic appliance on the patient's teeth and electrically coupling a pair of electrical contacts within the teeth-receiving cavities with a first node and a second node of an electrical trace on the patient's teeth, so that the electrical trace closes the electrical circuit; and emitting a signal when the electrical trace closes the electrical circuit indicating compliance.

Any of these methods may include storing the signal, and/or periodically emitting signals while the electrical trace closes the electrical circuit. Emitting the signal may comprise wirelessly transmitting the signal. The methods may also include logging the signal to track patient compliance.

For example, described herein are removable orthodontic devices including a biosensor. In some variations, the biosensor may be a bio sensor system that is configured to detect a biomarker that indicates a phase of movement of the patient's teeth during an orthodontist treatment. For example, the biosensor may be configured to detect one or more biomarkers, such as one or more salivary proteins, the expression of which changes during orthodontic treatment. As a non-limiting example, protein S100-A9 (S100 calcium-binding protein A9 or Calgranulin-B), serum albumin precursor, immunoglobulin J chain, immunoglobulin J chain, and Ig alpha-1 chain C region each show down-regulation two weeks (fourteen days) following the start of an orthodontic treatment. These markers may be in saliva or in GCF. Similarly, expression of IL-6, IL-8 levels in gingival crevicular fluid may be altered after force application is applied and remodeling has begun. The levels of markers for inflammation, remodeling and/or enzymes associated with bone resorption, formation, cell necrosis, collagen remodeling, etc. may be detected and may be associated with the phase of tooth movement.

Tooth movement induced by orthodontic force application may be characterized by remodeling changes in the dental and periodontal tissues and may include deflection, or bending, of the alveolar bone and remodeling of the periodontal tissues, including the dental pulp, periodontal ligament (PDL), alveolar bone, and gingiva. The applied force causes the compression of the alveolar bone and the PDL on one side, while on the opposite side the PDL is stretched.

Orthodontic tooth movement may be described as having three or more phases. For example, tooth movement may have an initial phase, a lag phase, and a post-lag phase. The initial phase may be characterized by immediate and rapid movement and may occurs 24 hours to 48 hours after the first application of force (above a movement threshold) to the tooth. This rate is largely attributed to the displacement of the tooth in the PDL space. The lag phase may typically last for 20 to 30 days, depending on the amount of force applied, and may show relatively little to no tooth displacement. This phase may be marked by PDL hyalinisation in the region of compression. Subsequent tooth movement typically does not occur until the cells complete the removal of all of the necrotic tissues. The postlag phase follows the lag phase, during which the rate of movement may again increase.

Thus, a removable orthodontic devices including a biosensor may include: a plurality of tooth receiving cavities configured to receive a plurality of teeth and to exert one or more orthodontic repositioning forces on the plurality of teeth; and at least one biosensor system comprising: a bioreceptor configured to cause a first interaction with one or more tooth motion biomarkers in fluid in the oral cavity, the first interaction being related to a first biomarker expression change of the one or more tooth motion biomarkers, and the first biomarker expression change being associated with a specific phase of tooth movement of the plurality of teeth;

and a biotransducer coupled to the tooth motion bioreceptor, the biotransducer configured to transduce the first interaction into a first interaction signal representative of the first interaction.

The specific phase of tooth movement may correspond to a velocity of root movement of roots of the plurality of teeth. For example, the level of the biomarker may reflect the velocity of the root movement. In some variations, if the velocity of root movement is substantially zero, the biosensor may indicate that a particular portion of an orthodontic treatment plan may be terminated, and a new stage (e.g., a new aligner, such as the next aligner in a sequence) may be applied.

Additional biomarkers may be used, including biomarkers that reflect changes indicative of other stages of tooth movement and/or of the presence and/or absence of the apparatus in the patient's mouth (e.g., compliance). For example, the bioreceptor may be configured to cause a second interaction with one or more compliance biomarkers, the second interaction being related to a second biomarker expression change associated with compliance by the patient; and the biotransducer may be configured to transduce the second interaction into a second interaction signal representative of the second interaction.

Any of the bio sensor systems described herein may include one or more processor configured to process the first interaction signal into sensor data used to provide one or more recommendations to change the removable orthodontic appliance at a specified time. The one or more processors may monitor the level of the biomarkers over time, and may store, analyze and/or transmit these levels. In some variation the one or more processors may compare the signal strength to a threshold; when the biomarker signal falls above (or in some variations, below, depending on the biomarker), the processor may indicate that the dental appliance should be removed and/or changed. As mentioned above, the at least one biosensor system may include one or more of: a memory, a power source, a communication unit, and an antenna.

Any of these systems may include a biosensor housing formed from at least a portion of the plurality of tooth receiving cavities and being configured to physically couple the bioreceptor to at least one tooth of the plurality of tooth. The bioreceptor may include a protein that selectively binds to the tooth motion biomarker (e.g., an antibody or antibody fragment, enzyme, etc.). For example, the bioreceptor may include a protein (e.g., one or more of a primary and/or a secondary protein). The bioreceptor may comprises an enzyme that selectively acts on the tooth motion biomarker.

The fluid may be saliva, gingival cervicular fluid (GCF), etc. In some variations, the tooth movement biomarker is one or more of: Calgranulin-B, Serum albumin precursor, Immunoglobulin J chain, Ig alpha-1 chain C region, Cysteine-rich secretory protein 3 precursor (CRISP-3), Hemoglobin subunit beta, Stratifin, and soluble RANK Ligand (sRANKL). The removable orthodontic device of claim 1, wherein the fluid comprises gingival crevicular fluid (GCF). In some variations, the tooth movement biomarker is one or more of: prostaglandin E2, Substance P, epidermal growth factor, transforming growth factor, Receptor activator of nuclear factor kappa-B ligand (RANKL), Granulocyet macrophage colony stimulation factor, α2 microglobulin, Interleukin 1β, Myeloperoxidase, hyaluronic acid and Chondroitin sulfate.

In any of the apparatuses (e.g., removable orthodontic devices, etc.) described herein, the apparatus may gather a baseline level of the biomarker. For example, the a baseline may be detected from the patient by having the patient wear a first removable orthodontic device that is not configured to move the teeth prior to wearing an orthodontic device that is configured to move the teeth. The first (baseline gathering device) may be worn for any appropriate time (e.g., 5 minutes or more, 1 hour or more, 2 hours or more, 3 hours or more 4 hours or more, six hours or more, 12 hours or more, 1 day or more, 3 days or more, one week or more, two weeks or more, etc.) for some minimum amount of time (5 minutes, 1 hour, 2 hours, 3 hours, 4 hours, 6 hours, 12 hours, 1 day, 3 days, 1 week, 2 weeks, etc.). This first device may be configured to rest on the teeth without applying any substantial moment (force) to move the teeth. The biosensor(s) on the device may therefore collect patient-specific baseline information that may be stored, analyzed and/or transmitted for use in the subsequent appliances (e.g., removable orthodontic devices) that are configured to move the teeth. For example in some variations, a series of appliances (removable orthodontic devices, e.g., aligners) may be worn in a sequence to move the teeth. Each subsequently-worn appliance that includes a biosensor system may collect the baseline information (e.g., baseline level of the one or more biomarker) by receiving this information collected from the initial device. This information may be transmitted to the subsequent removable orthodontic device(s) by the initial device and/or by a remote processor that communicates with the removable orthodontic device (e.g., wirelessly). Alternatively or additionally, the baseline information may be transmitted and stored remotely and comparisons to the baseline may be made remotely as well.

In some variations the apparatus (e.g., the removable orthodontic device) may include a biosensor reference. For example, the at least one biosensor system may include a reference electrode comprising the biotransducer material but not a bioreceptor material.

In some variations the bio sensor comprises one or more of nanowires and nanoparticles. In some variations, the biosensor comprises a conductive ink and an elastomeric binder. The elastomeric binder may include: silicone, fluorine rubber, polyurethane and isoprene block co-polymers. The biosensor may include a conductive substrate to which the biotransducer is attached and an insulating layer.

Some of the apparatuses (including a removable orthodontic device) may have multiple biosensors thereon. For example, in some variations the at least one biosensor system is one of a plurality of biosensor systems operably coupled to different portions of the removable orthodontic device.

Any of these apparatuses (e.g., removable orthodontic devices) described herein may also include a physical sensor operatively coupled to the removable orthodontic device, wherein the physical sensor is configured to sense one or more of a force, a pressure, a temperature, or a movement of the plurality of teeth.

As mentioned above, any of these methods may also include a communication module configured to transmit (e.g., wirelessly) the sensor data to a remote device.

The methods described herein may also include a method comprising: receiving a plurality of teeth in an oral cavity of a patient with a plurality of tooth receiving cavities of a removable orthodontic aligner, the plurality of tooth receiving cavities configured to exert one or more orthodontic repositioning forces on the plurality of teeth; placing a bioreceptor in contact with fluid in the oral cavity to cause a first interaction with one or more tooth motion biomarkers in the fluid, the first interaction being related to a first biomarker expression change of the one or more tooth motion biomarkers, and the first biomarker expression change being associated with a specific phase of tooth movement of the one or more teeth; transducing the first interaction into a first interaction signal representative of the first interaction; and providing the first interaction signal.

A removable orthodontic device as described herein may include: means for receiving a plurality of teeth in an oral cavity of a patient and to exert one or more orthodontic repositioning forces on the plurality of teeth; and at least one bio sensor system comprising: means for causing a first interaction with one or more tooth motion biomarkers in fluid in the oral cavity, the first interaction being related to a first biomarker expression change of the one or more tooth motion biomarkers, and the first biomarker expression change being associated with a specific phase of tooth movement of the plurality of teeth; and means for transducing the first interaction into a first interaction signal representative of the first interaction.

BRIEF DESCRIPTION OF THE DRAWINGS

In FIG. 3A a biosensor is shown coupled or integrated with the apparatus.

FIG. 6A is an example of an apparatus including an electrical trace that is bonded directly to the subject's teeth and configured to interact with electrical circuitry and/or power on a wearable orthodontic piece (e.g., aligner). In this example, wearing the aligner properly on the teeth completes a circuit in the aligner that may accurately trace compliance and/or may activate a sensor (e.g., biosensor). FIG. 6B illustrates the open circuit between the appliance (e.g., aligner, on left) and conductive traces on teeth when the appliance is not worn on the teeth or is improperly worn. FIG. 6C shows the closed circuit, when the appliance is worn so that the nodes on the teeth are coupled to the nodes on the appliance.

FIG. 7A is an example of a dental apparatus configured as a dental aligner that includes a biosensor monitoring apparatus. In this example, the biosensor includes a swellable material that swells when binding to one or more biomolecules. Swelling (and therefore binding to the biomarker(s) may be detected by detecting a pressure change in the material. FIGS. 7B and 7C schematically illustrate the biosensor portion of FIG. 7A, showing swelling of the swellable material (e.g., gel) before (FIG. 7B) and after (FIG. 7C) binding to the target biomarker.

FIGS. 10C-10H illustrate the operation of a biosensor similar to that shown in FIG. 10B, sampling over different time points.

FIG. 11 is example of another variation of an example of a bio sensor including microfluidics and assay chambers that may be operated in a chronological order to provide controlled sampling.

DETAILED DESCRIPTION

Described herein are methods and apparatuses for detecting a biomarker in the intraoral cavity. In particular, these methods and apparatuses may be configured to detect one or more biomarker, or a biomarker and a physiological marker (such as body temperature, blood oxygenation, galvanic skin response) including, but not limited to, detection from saliva or gingival crevicular fluid (GCF).

For example, a generic apparatus as described herein may include a sensor (e.g., biosensor) configured to be positioned in a subject's oral cavity and an electronics system in communication with the sensor, where the electronic system includes one or more of: a signal amplifier, a signal conditioner (e.g., filter, averaging, etc.), processor, memory (e.g., data logging unit), power source (e.g., battery, capacitor, etc.) and data communications (e.g., wired or wireless communications, such as Bluetooth, Wifi, Zigbee, RFID, ultrasound, or the like). The sensor typically converts a biomarker detection into an electrical signal, and may include a bioreceptor and a biotransducer. The bioreceptor is configured to interact with a specific analyte or subset of analytes and produce a measurable signal (optical, chemical, mechanical, thermal, electrical, or some combination of these) that is transduced by the biotransducer into an electrical signal that can be processed (amplified, filtered, averaged, combined, etc.) by the electronic subsystem. The electronic subsystem may be an integrated system (e.g., a CMOS-based microprocessor). All or some of these components may be on or part of an oral appliance, such as an aligner, brace, palatal expander, etc.

Figure 3A:
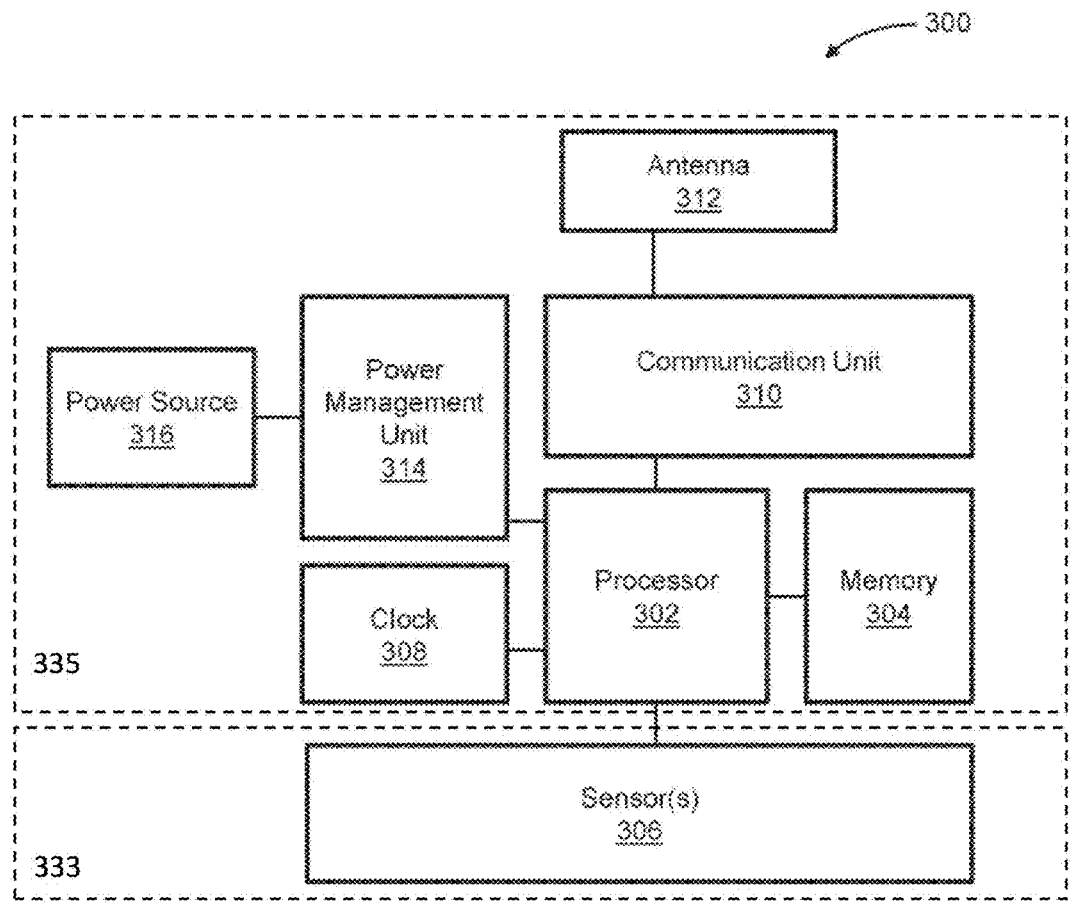
FIG. 3A schematically illustrates one example of an apparatus including a monitoring device (e.g., electronics) that may include a biosensor or may communicate with a biosensor coupled to the oral cavity (e.g., teeth, gingiva, etc.).

For example, FIG. 3A shows a portion of an apparatus that includes a bio sensor (sensor(s) 306) comprising a bioreceptor and biotransducer, in communication with an electronics system 335. The biosensor may be integrated and/or incorporated with the electronics system 335 and connected directly to a patient, etc., on a tooth, teeth, gingiva, etc., or it may be connected to an oral appliance. The biosensor(s) 333 may be separate from the electronics system 335 (indicated by the dashed lines. For example, the biosensor(s) may be part of a second oral appliance and/or directly mounted in the oral cavity (e.g., on a tooth/teeth), and may couple to an oral appliance including all or some of the electronics system (e.g., battery/power source 316, processor 302, antenna 312, memory 304, etc.).

Figure 3B:
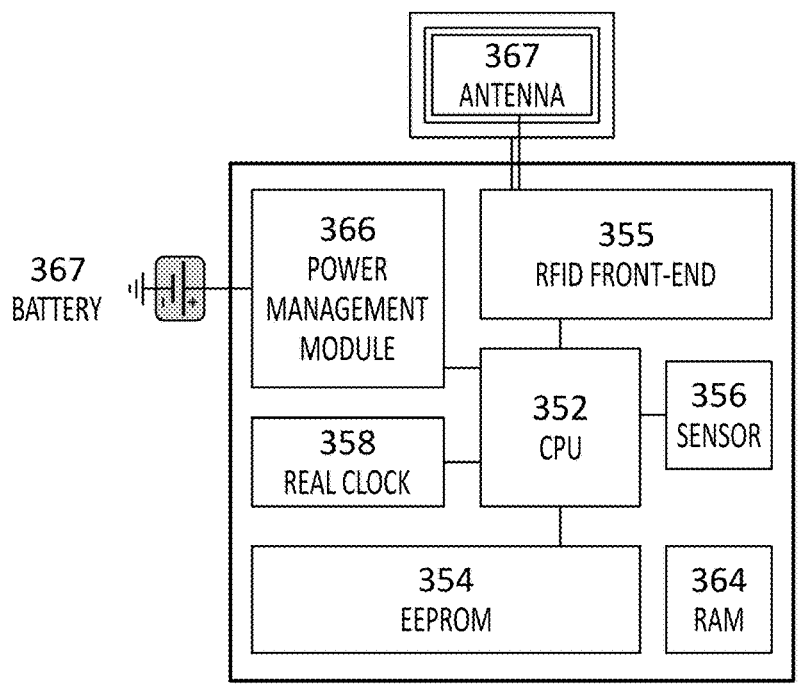
FIG. 3B schematically illustrates another example of an apparatus including a biosensor.

FIG. 3B is another example of a schematic illustrating a biosensor apparatus. In FIG. 3B, the biosensor(s) 356 are integrated with the electronics system. The electronics system in this example include a processor (CPU 352) that may amplify, filter, analyze and/or store the signals from the biosensor(s). The biosensor(s) may include a bioreceptor and a biotransducer that converts interaction (e.g., binding, enzymatic interaction, etc.) with a biomarker into an electrical signal. The electronics may further include an oscillator/clock 358, and a memory (e.g., EEPROM 354). Additional memory (e.g., RAM 364) may also be included. The memory may store data generated by the biosensor(s) and/or control logic/command logic for operating the apparatus. This logic may be modified (e.g., programmable). Additional memory the electronics system (which may also be referred to herein as a sensor electronics system or subsystem) may include communications circuitry (shown as an RFID front end 355) in FIG. 3B, which may also include or communicate with an antenna 357. The electronics system may also include power management circuitry 366, for regulating the power used by the electronics and/or biosensor(s). The power management circuitry may regulate a power source, such as a battery 367.

Figure 4A:
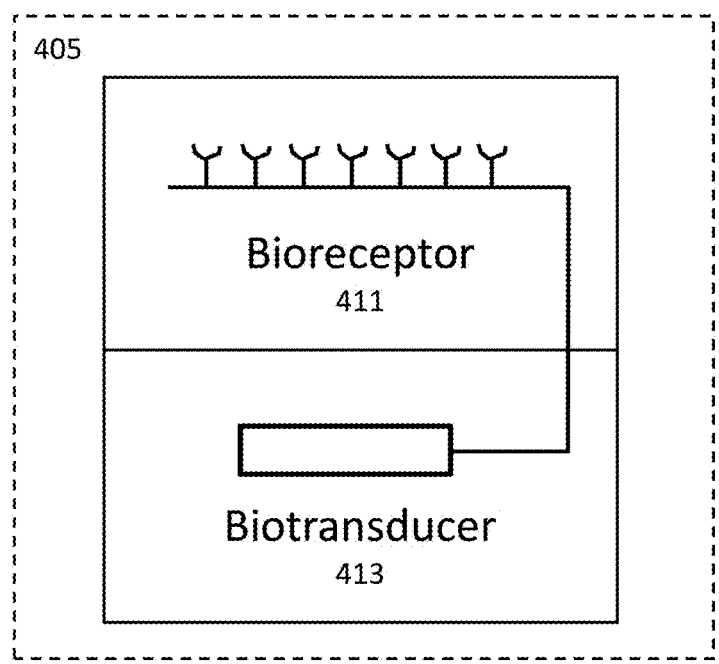
FIG. 4A illustrates a schematic of a biosensor apparatus (e.g., which may be part of a monitoring device) with an activation mechanism.

As schematically illustrated in FIG. 4A, a biosensors may include a bioreceptor 411 that interacts with a biomarker and is functionally coupled with a biotransducer 413. In this example, the bioreceptor is shown schematically including specific interaction sites that may engage with a biomarker, e.g., by binding, enzymatically reacting with, etc. The biotransducer 413 is functionally linked to bioreceptor and may transduce interaction between the biomarker and the bioreceptor into an electrical signal (output) that is passed on to the electronic system (not shown, see, e.g., FIGS. 3A and 3B). For example, the biotransducer may bind to the bioreceptor and binding may be detected by the biotransducer via an optical signal. In some variations, the bioreceptor may be bound to an optically transparent substrate through which light may be passed by the biotransducer; a change in the optical properties of the bioreceptor may correlate with binding of the biomarker to the biotransducer. Alternatively, the bioreceptor may include a matrix (e.g., hydrogel) that interacts with the biomarker to modify a property of the matrix (e.g., electrical resistance, optical absorption, electrochemical potential, etc., and this modified property may be polled and/or detected by the biotransducer. Other specific examples are provided below.

Figure 4B:
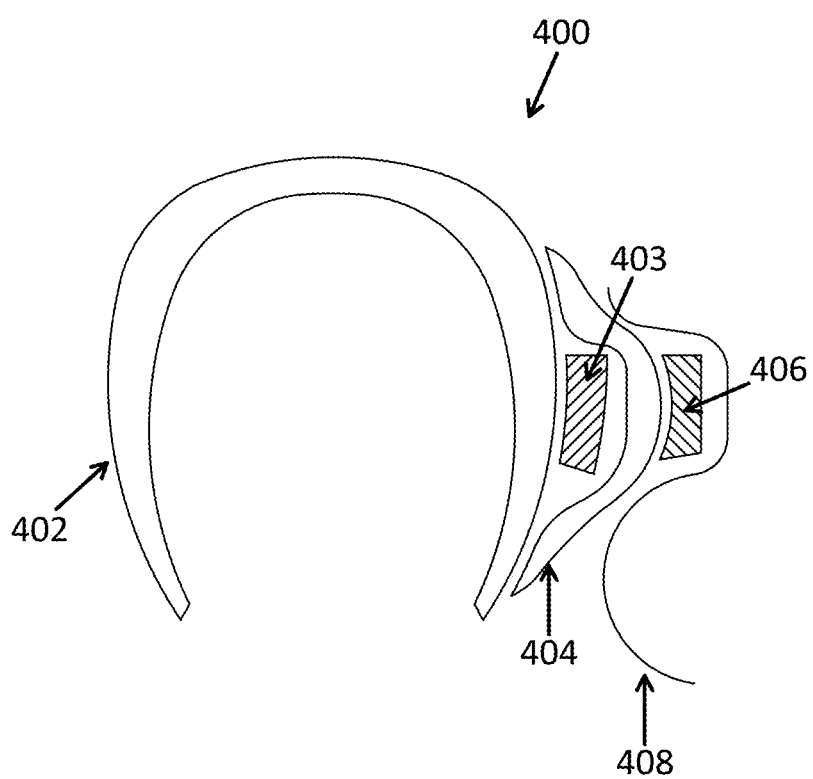
FIG. 4B illustrate schematically an example of a monitoring device 400 with an activation mechanism.
Figure 4C:
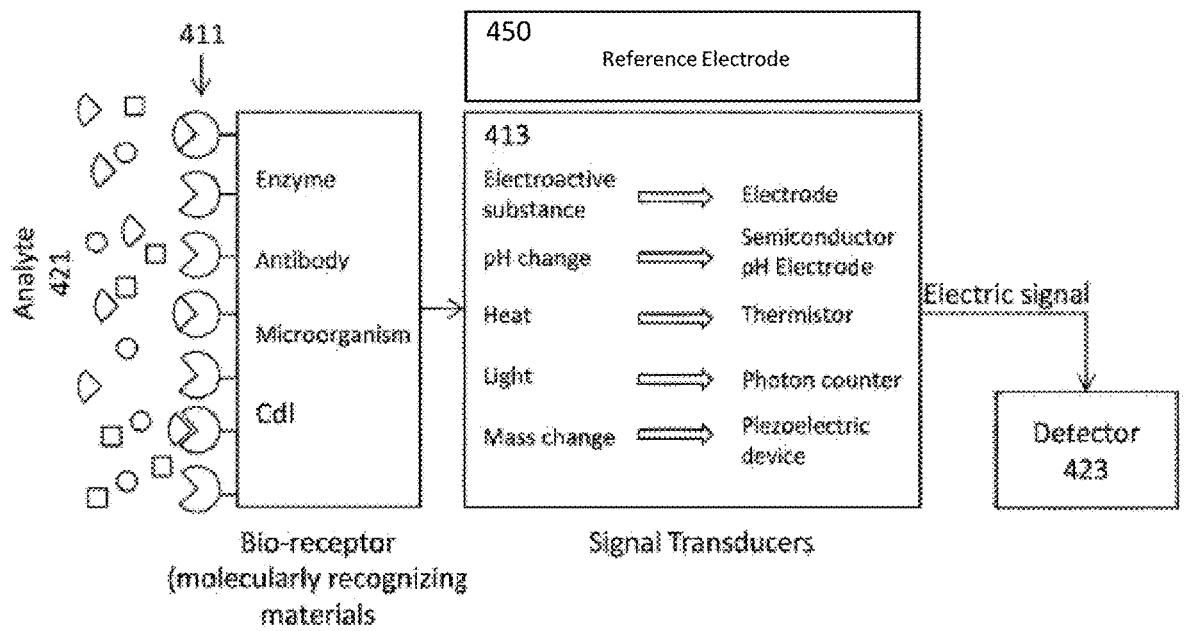
FIG. 4C schematically illustrates another example of an apparatus (e.g., including a monitoring device) configured as a biosensor with an activation mechanism.
Figure 4D:
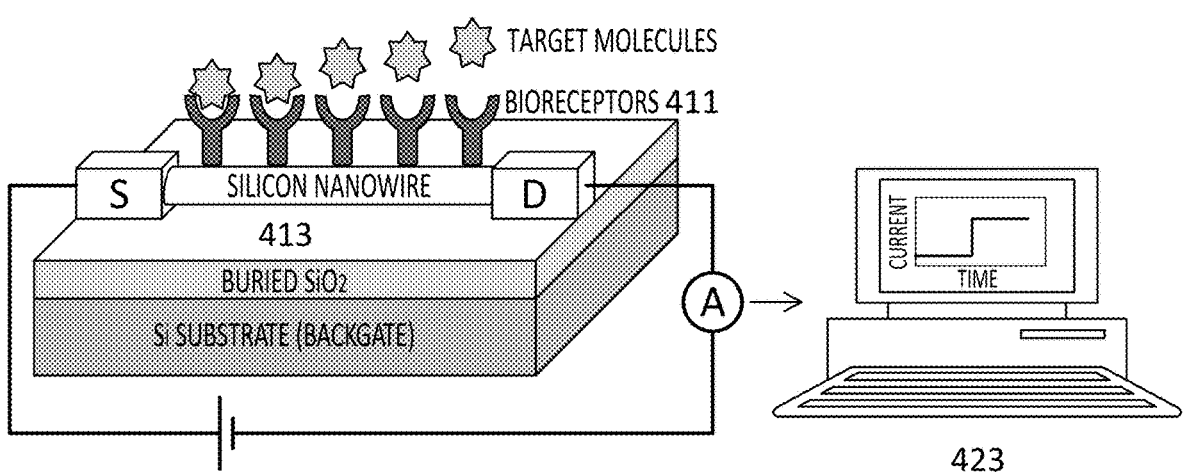
FIG. 4D is an example of an apparatus with an activation mechanism similar to that shown in FIGS. 4A and 4C. In this example, the apparatus includes bio-receptors formed on a silicon nanowire atop a substrate. Nanoparticles and/or nanowires may be used as part of the bio-receptor.

FIGS. 4C and 4D also illustrate examples of biosensors that include a bioreceptor 411 that interacts with a biomarker and is functionally coupled with a biotransducer 413. In FIG. 4C, analyte 421 is detected by specifically binding to a bioreceptor 411 (e.g., a molecularly recognizing material such as an enzyme, antibody, microorganism, Cdl, etc.) and this interaction is detected by the signal transductor forming the biotransducer 413 (e.g., an electroactive substance detected by an electrode, pH changing material detected by a pH electrode, an exothermic reaction being detected by a thermocouple, a photon-emitting reaction detected by a photon counter, a mass change detected by a piezoelectric device, etc.). Signals from the transducer are typically converted to electrical signals (analog and/or digital) that are then transmitted to a detector 423. The biosensor system may optionally include a reference electrode 450, as described herein.

Any appropriate biomarker or biomarkers may be used. Biomarkers may be biomolecules or byproducts of biomolecules that are present in the oral cavity (including saliva, GCF, and/or breath) and/or contaminants that may be present in the oral cavity, such as bacteria, yeast, etc. Biomolecules of particular interest include those that change in response to movement of the teeth due to an orthodontic procedure. For example, Table 1, below lists examples of biomarkers that may be tested using the biosensor apparatuses described herein. For example in Table 1, protein biomarkers include Protein S100-A9 (e.g., S100 calcium-binding protein A9, Calgranulin-B), Serum albumin precursor, Immunoglobulin J chain, Ig alpha-1 chain C region, Cysteine-rich secretory protein 3 precursor (CRISP-3), Hemoglobin subunit beta (Hemoglobin beta chain, Beta-globin), and 14-3-3 protein σ (Stratifin, Epithelial cell marker protein 1).

TABLE 1

Summary of saliva proteins with expression change during orthodontic treatment. (These are proteins that show statistically significant change ($P < 0.5$) between day 0 and day 14 of orthodontic treatment.)

| Spot no. | Protein name | Known Function | Accession number (UniProt) | MW (kDa)/pI Theoretical | MW (kDa)/pI Experimental | Peptides matched/% coverage (Protein score) | Expression change |
|---|---|---|---|---|---|---|---|
| 1 | Protein S100-A9 (S100 calcium-binding protein A9) (Calgranulin-B) | (i) Calcium-binding protein. (ii) Promotes phagocyte migration and infiltration of granulocytes at sites of wounding. | P06702 | 13.2/5.71 | 14.5/5.47 | 4/24% (121) | Down regulated at day 14 |

TABLE 1-continued

Summary of saliva proteins with expression change during orthodontic treatment. (These are proteins that show statistically significant change (P < 0.5) between day 0 and day 14 of orthodontic treatment.)

| Spot no. | Protein name | Known Function | Accession number (UniProt) | MW (kDa)/pI Theoretical | MW (kDa)/pI Experimental | Peptides matched/% coverage (Protein score) | Expression change |
|---|---|---|---|---|---|---|---|
| 2 | Serum albumin precursor | (iii) Plays a role as a proinflammatory mediator in acute and chronic inflammation. (i) Good binding capacity for water, Ca2+, Na+, K+, fatty acids, hormones, bilirubin, and drugs. (ii) Main function is the regulation of the colloidal osmotic pressure of blood. (iii) Major zinc transporter in plasma. | P02768 | 69.3/5.92 | 14.8/7.00 | 8/11% (105) | Down regulated at day 14 |
| 3 | Immunoglobulin J chain | (i) Serves to link two monomer units of either IgM or IgA. (ii) Help to bind IgM or IgA to secretory component. | P01591 | 15.5/4.62 | 34.0/3.86 | 10/30% (220) | Down regulated at day 14 |
| 4 | Immunoglobulin J chain | | P01591 | 15.5/4.62 | 36.4/3.40 | 6/27% (198) | Down regulated at day 14 |
| 5 | Ig alpha-1 chain C region | (i) Major immunoglobulin class in body secretions. (ii) Serve both to defend against local infection and to prevent access of foreign antigens. | P01876 | 37.6/6.08 | 44.76/6.91 | 9/20% (260) | Down regulated at day 14 |
| 6 | Cysteine-rich secretory protein 3 precursor (CRISP-3) | (i) Innate immune response (ii) Potential biological marker for prostate cancer | P54108 | 27.6/8.09 | 43.25/8.90 | 2/6% (94) | Present only at day 14 |
| 7 | Hemoglobin subunit beta (Hemoglobin beta chain) (Beta-globin) | Involved in oxygen transport from the lung to the various peripheral tissues. | P68871 | 15.9/6.75 | 14.83/9.50 | 6/27% (158) | Present only at day 0 |
| 8 | 14-3-3 protein σ (Stratifin) (Epithelial cell marker protein 1) | (i) Adapter protein. (ii) Binds to a large number of partners, generally results in the modulation of the activity of the binding partner. | P31947 | 27.7/4.68 | 44.76/4.20 | 5/22% (147) | Present only at day 0 |

Table 1: Gingival Crevicular Fluid (GCF) biomarkers (Table 1 is adapted from Ellias MF et al. "Proteomic Analysis of Saliva Identifies Potential Biomarkers for Orthodontic Tooth Movement". *The Scientific World Journal*. 2012; 2012:647240. doi:10.1100/2012/647240.)

Any of the apparatuses and methods described herein may target biomarkers present in gingival cervicular fluid (GCF). In general, various molecules are capable of passing through gingival sulcular epithelium and may filter into GCF. Many of these molecules are associated with remodeling of paradental tissues during situations such as normal maintenances, periodontal diseases and Orthodontic treatment. The collection and analysis of GCF is a non-invasive procedure that may be useful information on the nature and extent of the periodontal response to mechanotheraphy and orthodontic treatments. The apparatuses and methods described here may be configured and/or adapted to collect GCF. For example any of the apparatuses described herein may include a projection extending between the teeth and gingiva (e.g., penetrating to a depth of 0.5 mm, 1 mm, 2 mm, 3 mm, 4 mm, 5 mm, 6 mm, etc.). The projection may be fixed or extendable. The projection may include a capillary.

Modified or enhanced cellular activities during orthodontic tooth movement can be found in GCF of treated teeth. Additional biomarkers that may be examined, e.g., in GCF and/or saliva include prostaglandin E (PGE) (elevated prostaglandin E (PGE) levels in GCF 1 day after application of mechanical stimuli has been detected), cytokines, including IL-6 and IL-8, TNF-α, Hyaluronic acid, chondroitin sulphate, IGF, Acid phosphatase, Aspartate aminotransferase, Alkaline phosphatase (ALP), Lactate dehydrogenase, Collagenase, Matrix metalloproteinases (e.g., MMP-1, MMP-2 and MMP-8), Cathepsin B, TRAP, Osteocalcin, Osteonectin, Osteopontin and dentin sialoprotein. For example, a correlation has been found between the velocity of tooth movement and increase in concentrations of cytokine and its receptor antagonist. IL-6, IL-8 levels in GCF after force application has been shown. Increased level of TNF-α in GCF after force application which peaked at day 1 has been shown. Studies demonstrated elevated Hyaluronic acid in all GCF samples and chondroitin sulphate levels in GCF increased greatest in teeth that moved most. IGF (bone remodeling marker) may be elevated, and its binding protein levels in GCF, 4 h after mechanical stimulation. Acid phosphatase and Aspartate aminotransferase levels after force application are higher on compressed side compared to tension side in GCF. Alkaline phosphatase (ALP) levels are higher on tension side compared to compression side. Lactate dehydrogenase levels are higher on compression side whereas Collagenase levels are elevated on both mesial and distal sides after mechanical stimulus. Matrix metalloproteinases (MMPs) (MMP-1, MMP-2 and MMP-8) show elevated levels on compressed side than on tension side. Elevated levels of Cathepsin B, an indicator of ECM degradation, were demonstrated in GCF 1 day after force application. Elevated levels of TRAP in GCF on the compression side after force application has been shown. Osteocalcin, a bone turnover marker, may be elevated in GCF of patients with periodontal breakdown. Elevated levels of Osteonectin and Osteopontin have been detected in GCF with progressive increase in periodontal breakdown. Elevated levels of dentin sialoprotein in GCF samples of teeth at 12 weeks following commencement of fixed appliance therapy have also been demonstrated.

For example, the apparatuses and methods described herein may be configured to detect one or more of the following biomarkers. In some variations, these biomarkers may be detected from the saliva and/or the gingival crevicular fluid (GCF). These biomarkers may be particularly helpful in detecting tooth remodeling or movement. The levels of one or more of these biomarkers may be detected and tracked over the course of a treatment to adjust or modify an orthodontic treatment. For example, one of more markers for inflammation, remodeling and/or enzymes (e.g., enzymes associated with bone resorption, formation, cell necrosis, collagen remodeling, etc.) may be detected. Examples of makers for remodeling of the teeth may include: Glycosaminoglycans (e.g., in GCF), including hyaluronic acid and a minor band of chondroitin sulfate, Pyridinium derivatives (e.g., pyridinoline and deoxypyridinoline), Pentraxin-3, also known as tumor necrosis factor (TNF)-stimulated gene 14 (TSG-14), N-telopeptide type 1 and osteocalcin, Osteocalcin, and Matrix metalloproteins (MMPs) 1 and 8. Markers for inflammation may include: Prostaglandin E (PGE2), Neuropeptides (calcitonin related gene peptide and substance p), Transforming growth factor-α1, Epidermal growth factor (EGF), α2 Microglobulin (α2MG), insulin-like growth factor-1, Interleukin-1 (receptor antagonist) (IL-1) 1β, 2, 6, 8 cytokines, Tumor necrosis factor-α, Macrophages colony stimulating factors, TNF-related ligand receptor activator of nuclear factor-kappa ligand (RANKL) and its two receptors, receptor activator of nuclear factor-kappa (RANK), and osteoprotegerin (OPG), and Myeloperoxidase (MPO). Markers of root resorption may include: dentine matrix protein 1, dentin phosphoprotein (DPP), and dentin sialoprotein (DSP). Enzymes and enzyme inhibitors may include: Cathepsin B, Acid phosphatase (ACP) and alkaline phosphatase (ALP), (3-Glucuronidase (βG), Aspartate aminotransferase (AST), and lactate dehydrogenase.

As mentioned above, any of the bio sensors described herein may include a bio-recognition component, a biotransducer component, and electronic system which may include a signal amplifier, processor, data logging units and data communication unit. In some instances, transducers and electronics can be combined such as in CMOS-based microsensor systems. The recognition component may be called a bioreceptor, may use a biomolecule from organisms or receptors modeled after biological systems to interact with the analyte of interest. This interaction may be measured by the biotransducer which outputs a measurable signal proportional to the presence of the target analyte in the sample. The processor can log the raw or processed data in the memory unit or transmit it to a receiver. The system can work actively if energized with battery, super-capacitor, or an energy harvesting unit, or it may perform passively upon being energized via induction using an external device, such as cell phone.

In any of the biosensors described herein, the bioreceptor may be configured to interact with the specific analyte of interest to produce an effect measurable by the transducer. The bioreceptor may have a high selectivity for the analyte among a matrix of other chemical or biological components. While the type of biomolecule used may vary widely, biosensors may be classified according to common types of bioreceptor interactions involving, e.g., interactions such as: antibody/antigen, enzymes/ligands, nucleic acids/DNA, cellular structures/cells, or biomimetic materials. The bioreceptor may be configured to engage in one or more of these interactions (e.g., may include a bound or engineered antibody, enzyme, nucleic acid sequence, protein or engineered protein, etc.) in a localized manner that may be interrogated by or communicated to the biotransducer.

For example, a biosensor as described herein for use with an oral appliance may be configured to take advantage of an antibody/antigen interaction with one or more of the biomarkers described herein. Thus, the biosensor may be configured as an immunosensor. An immunosensor may utilize the very specific binding affinity of antibodies for a specific compound or antigen. The specific nature of the antibody antigen interaction is analogous to a lock and key fit in that the antigen will only bind to the antibody if it has the correct conformation (proper selection of primary and secondary antibodies). Binding events result in a physicochemical change that, in combination with a tracer, such as fluorescent molecules or enzymes, can generate a signal such as an elevation in voltage that can be detected by electronic components. Binding may be detected optically (e.g., by color, or transmission) and/or electrically.

Also described herein are biosensors that include enzymatic interactions. For example, analyte recognition may be enabled through: (1) an enzyme converting the analyte into a product that is sensor-detectable, (2) detecting enzyme inhibition or activation by the analyte, or (3) monitoring modification of enzyme properties resulting from interaction with the analyte. Since enzymes are not consumed in reactions, the biosensor may be used continuously. The catalytic activity of enzymes may also lower limits of detection compared to common binding techniques.

Other biosensing techniques that can be used may include detecting nucleic acid interactions, detecting epigenetic modifications, cell based, and tissue based detection.

As mentioned above, a biotransducer may be electrochemical, optical, electronic, piezoelectric, gravimetric, and/or pyroelectric-based.

Figure 5A:
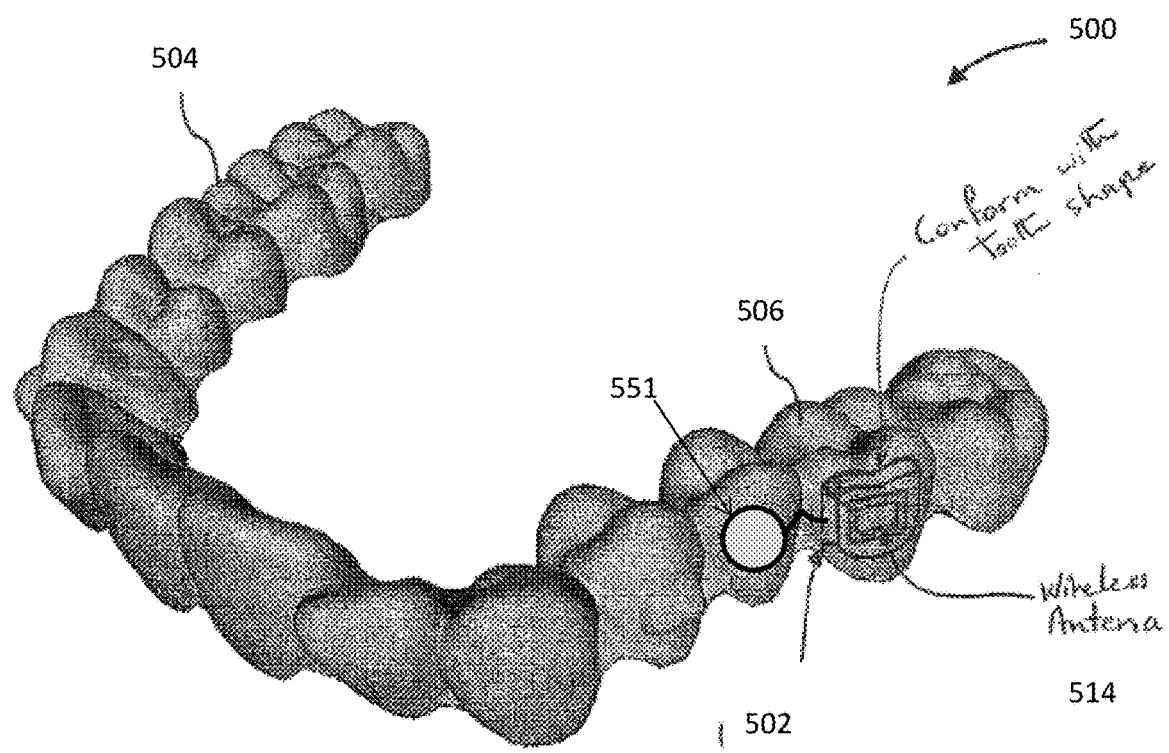
FIG. 5A illustrates an example of a dental apparatus (e.g., a removable orthodontic device, also referred to as an orthodontic appliance) including an integrated monitoring device.
Figure 5B:
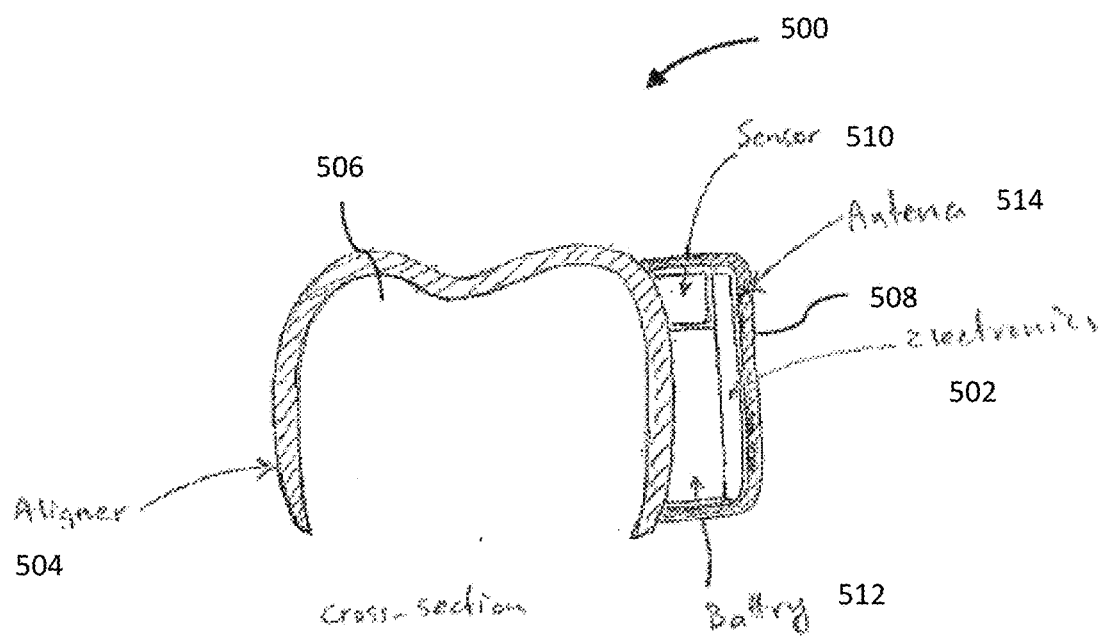
FIG. 5B is a cross-sectional view of the appliance of FIG. 5A.

FIGS. 5A and 5B illustrate an example of an apparatus including a biosensor as described herein. For example, In FIG. 5A, the apparatus 500 includes an orthodontic device, shown as an aligner 504 to which a biosensor or biosensors are coupled, either integrated into the housing of the electronics sub-assembly 502, or separate 551 but electrically connected to the electronics. The electronics (processor, battery, communications circuitry, antenna, etc.) is shown in a housing that mounted to an outside portion of the aligner, shown on the buccal side, although it may be on the lingual side instead or additionally. FIG. 5B shows an example of a section through an example of the apparatus in which the bio sensor (or a separate sensor 510, such as a temperature sensor or the like) is included with the electronics 502. An outer cover 508 may hold the assembly to the aligner 504 and the apparatus may be placed over the teeth 506. In some variations the electronics and/or sensor are on the inner surface of the aligner (e.g., the cavity into which the teeth sit.

In addition to the biosensors described above, also described herein are sensors configured to determine stress-induced bioelectric potentials on the teeth. Stress-induced bioelectric potentials may regulate alveolar bone remodeling during orthodontic tooth movement. For example, the force, F, applied to the labial surface of the lower incisor that displaces the tooth in its socket, deforming the alveolar bone convexly towards the root at the leading edge, may produce concavity towards the root at the trailing edge. Concave bone surfaces characterized by osteoblastic activity are electronegative; convex bone surfaces characterized by osteoclastic activity are electropositive or electrically neutral. Measuring the electrical charge on the teeth surface, may be used to determine the tooth movement rate and direction. Such data can be used to conduct a closed-loop orthodontic treatment. For example, any of the methods an apparatuses described herein may measure or detect the electrical charges from the surface of different regions of a subject's teeth. An apparatus may include a plurality of electrodes within the concavity of an aligner, or a plurality of electrical contacts for contacting electrodes attached to the teeth, e.g., attached to one or both of the buccal and lingual sides of any of the teeth that are being moved by the orthodontic appliance. The apparatus may include the electrical system that is configured to receive these surface charge readings and may store, transmit (e.g., wireless) or analyze these signals, e.g., in the electrical system or remotely, to determine and/or evaluate forces on the teeth and tooth movement.

Also described herein are systems and apparatuses for determining one or more indicator of the patient's heath. For example, any of these methods and apparatuses may include a sensor configured as a physiological sensor to detect one or more subject physiological state. For example, any of the apparatuses or methods described herein may measure (e.g., using a physiological sensor) one or more of: electrocardiogram (ECG), bio-impedance, blood oxygenation, galvanic skin response, heart rate, body temperature, respiration (including respiration rate), or the like. For example, any of these apparatuses may include an ECG sensor (e.g., one-point ECG electrode), a thermistor, a bio-impedance sensor, a photoplethysmogram sensor, a galvanic skin response sensor, etc., including electronics to support such sensor(s). These sensors can be utilized by themselves or with any other sensor, including one or more of the biosensors described herein. As with any of the biosensors and sensors described herein, these sensors may be used to detect or determine compliance (e.g., use of the aligners) while they generate health information of the patient. For instance, a photoplethysmogram (PPG) sensor may measure blood-volume changes in the blood tissue. A plethysmogram is volumetric measurement of an organ. This technique is non-invasive and may be obtained by illuminating light into the body and measuring the change in light absorption. In the current invention, this technique may be applied within the intraoral cavity. A plethysmography sensor can be incorporated in an orthodontic appliance (e.g., aligner) to determine the blood volume change in a cheek or within an extended gingiva segment near or under the appliance to detect blood volume change in gingiva.

Alternatively or additionally, a galvanic skin response (GSR) sensor may be used to measure conductivity of intraoral tissues. Conductivity may change with both changes in the underlying amount of minerals released onto the outer surface of tissues from glands.

Also described herein are methods and apparatuses for detecting and/or analyzing breath. For example any of the apparatuses described herein may be used to detect and/or diagnose disease. For instance, lung and breath cancers may be detected via analysis of the breath, e.g., by identifying particular breath volatile organic compounds (BVOCs) that differ between patients with non-small cell lung cancer (NSCLC) and subjects without the disease. Other sensors that detect cancer at early stages via, for instance, measuring chemical components of breath during exhale. Exhaled breath contains both volatile and non-volatile organic compounds, which vary between healthy individuals and those with lung cancer.

The apparatuses and methods described herein may also be configured to detect halitosis (bad breath). Halitosis may arise from inside the mouth and/or due to a disorders in the nose, sinuses, throat, lungs, esophagus, or stomach. Bad breath may also be due to an underlying medical condition such as liver failure or ketoacidosis. Halitosis may also arise from an underlying disease such as gum disease, tooth decay, or gastroesophageal reflux disease.

By far the most common causes of halitosis are odor producing biofilm on the back of the tongue, below the gum line, and in the pockets created by gum disease between teeth and the gums. This biofilm results in the production of high levels of foul odors produced mainly due to the breakdown of proteins into individual amino acids, followed by the further breakdown of certain amino acids to produce detectable gases. Volatile sulfur compounds are associated with oral malodor levels, and usually decrease following successful treatment. The intensity of bad breath may differ during the day, due to eating certain foods (such as garlic, onions, meat, fish, and cheese), smoking, and alcohol consumption. The odor may be worse upon awakening and may be transient or persistent (e.g., chronic bad breath).

The apparatuses and methods described herein may be configured to detect one or more compounds or markers for bad breath (e.g., above a target threshold) that may indicate bad breath, and may alert the wearer, track, store, and/or transmit detected levels. Markers that may be detected by the apparatuses described herein may include indole, skatole, polyamines, volatile sulfur compounds (VSCs) such as hydrogen sulfide, methyl mercaptan, allyl methyl sulfide, and dimethyl sulfide. In some variations the apparatus may detect one or more bacterial markers arising due to halitosis-producing bacteria. Bacteria that cause gingivitis and periodontal disease (periodontopathogens) may be gram negative may produce VSC. Methyl mercaptan is known to be a contributing VSC in halitosis that and may be caused by periodontal disease and gingivitis.

These apparatuses may also be used to determine, detect and/or diagnose other dental issued, including gum disease. For example, the level of VSC on breath has been shown to positively correlate with the depth of periodontal pocketing, the number of pockets, and whether the pockets bleed when examined with a dental probe. VSC may themselves contribute to the inflammation and tissue damage that is characteristic of periodontal disease. Markers for halitosis may also suggest or indicate infection (e.g., oral infection), oral ulceration, stress/anxiety, menstrual cycle (e.g., at mid cycle and during menstruation, increased breath VSC has been reported), or the like. Any of the methods and apparatuses described herein may also or alternatively be used to detect or determine (and/or aid in treatment) of any of these indications.

For example, a dental apparatus including a sensor may be configured to detect sulfide (e.g., sulfur emissions) from the patient's breath, saliva and/or GCF. For example, the sensor may be configured to detect hydrogen sulfide. Alternatively or additionally, the apparatus may be configured to detect methyl mercaptan, and dimethyl sulfide. In some variations the sensor may be configured to detect a salivary levels of an enzyme indicating the presence of certain halitosis-related bacteria, such as β-galactosidase.

Any of the apparatuses described herein may include microfluidics (e.g., lab-on-a-chip) components. Microfluidics may be used as part of the biosensor, for example, including channels for acquiring a biological fluid (e.g., saliva and/or GCF), processing the fluid (e.g., combining with one or more reagents and/or detecting an interaction with a biomolecule, etc.).

Also included herein is the use of one or more biosensors (e.g., integrated with an orthodontic appliance such as an aligner) to detect either a protein or DNA component of an allergen. See, e.g., Alves et al., describing a biosensor system for food allergen detection (e.g., Alves et al. 2015. DOI: 10.1080/10408398.2013.831026). As described herein, biosensors are well-suited to automation and their ability to detect multiple analytes in one test with minimal sample preparation and may be used to conduct in vivo detection and detect the presence of food allergens in close to real-time. For example, surface plasmon resonance (SPR)-based biosensors, typically used to the fast detection of egg-related fining allergens in wines, can be integrated with any of the orthodontic appliances (e.g., aligners) described herein to allow rapid detection the presence of egg white allergens at concentrations between 0.03 and 0.20 µg/mL.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

In general, the methods and apparatuses described herein may be used for monitoring the progress of appliance-based orthodontic treatment and/or compliance. Generally, a monitoring apparatus may include one or more biosensors and/or sensors (e.g., physiological sensors) configured to generate sensor data; this data may be related to repositioning of a patient's teeth using an orthodontic appliance. The biosensor and/or sensor data can be processed and analyzed to determine whether the appliance is successfully repositioning the teeth according to prescribed treatment plan. Advantageously, also described herein are integrated electronic sensing and logging systems capable of generating more reliable and accurate aligner performance data, which may be used by the treating practitioner to track treatment progress and adjust the patient's treatment plan if desired. The monitoring devices of the present disclosure can provide high value sensing data useful for adaptive closed-loop treatment planning and appliance design.

Monitoring performance of an orthodontic appliance for repositioning a patient's teeth is described. The apparatus can comprise an orthodontic appliance comprising one or more teeth-receiving cavities shaped to reposition the patient's teeth from an initial arrangement towards a target arrangement. The device can comprise one or more sensors configured to generate sensor data related to the repositioning of the patient's teeth by the orthodontic appliance. The device can comprise a processor configured to process the biosensor/sensor data in order to evaluate the performance of the orthodontic appliance in effecting the repositioning of the patient's teeth.

The performance of the orthodontic appliance can be measured in a variety of ways. For example, the processor may be configured to evaluate the performance of the orthodontic appliance by using the biosensor and/or sensor data to determine one or more of: an amount of force or pressure applied to the patient's teeth, a distribution of force or pressure on the patient's teeth, an amount of movement of the patient's teeth, or a movement rate of the patient's teeth, and/or the phase of movement of the patient's teeth (e.g., initial phase, a lag phase, and a post-lag phase, etc.).

The performance of the orthodontic appliance can determine one or more of: determining if movement is happening, what phase of tooth movement the patient is experiencing, and/or the rate of tooth movement. This information may be processed on the orthodontic appliance itself or off of the appliance (in a remote processor, etc.) and communicated to the dental professional and/or patient. This information may be used to adjust the treatment plan, including instruction removal of an orthodontic appliance (e.g., a removable orthodontic appliance/device) ahead of a scheduled removal, leaving the orthodontic appliance on longer than a scheduled removal date, or maintaining the scheduled removal/replacement date. In some variations the information (e.g., the information derived by monitoring the level of one or more biomarkers using the biosensors) may be used to modify the treatment plan by triggering replacement of one or more devices (aligners) within a planned sequence of removable orthodontic appliances.

In addition to the biosensors described herein, any of these methods and apparatuses may include a force or pressure sensor configured to measure force or pressure applied to one or more teeth by the orthodontic appliance. A force or pressure sensor can comprise a force- or pressure-sensitive film, a resistive film, a capacitive film, or a piezoelectric tactile sensor. The processor can be configured to evaluate the performance of the orthodontic appliance by determining whether an amount of force or pressure applied to the patient's teeth by the orthodontic appliance is within a targeted range. Any of these sensors may be used in combination with one or more biosensor, e.g., to confirm or estimate movement of the teeth.

A movement sensor may be included and configured to measure movement of one or more teeth. A movement sensor can comprise an electromagnetic field generator configured to generate an electromagnetic field. A movement sensor can be configured to measure the movement of the one or more teeth by measuring changes to the electromagnetic field. For instance, a movement sensor can comprise one or more electromagnetic targets arranged to move in response to the movement of the one or more teeth, such that movement of the one or more electromagnetic targets produces changes to the electromagnetic field.

Any of the apparatuses described herein may include a plurality of different biosensor and/or sensors operably coupled to different portions of the orthodontic appliance. Any or all of these bio sensors/sensors can be integrated with the orthodontic appliance, coupled to a tooth, or a combination thereof. As discussed above, a processor may be integrated with the orthodontic appliance or coupled to a tooth. Alternatively, a processor can be located external to the patient's intraoral cavity. Any of these apparatuses my further comprises a communication module configured to transmit one or more of the sensor data or the processed sensor data to a remote device. In some variations, the voltage generated by the biosensor may be used to recharge the battery.

A method for monitoring performance of an orthodontic appliance for repositioning a patient's teeth may include receiving biosensor and/or sensor data related to the repositioning of the patient's teeth by the orthodontic appliance from one or more biosensors and/or sensors. The orthodontic appliance can comprise one or more teeth-receiving cavities shaped to reposition the patient's teeth from an initial arrangement towards a target arrangement. The biosensor data can be processed in order to evaluate the performance of the orthodontic appliance in effecting the repositioning of the patient's teeth.

Performance of the orthodontic appliance may be evaluated by using the biosensor data to determine one or more of: the state of a biomarker associated with tooth movement and/or remodeling, an amount of force or pressure applied to the patient's teeth, a distribution of force or pressure on the patient's teeth, an amount of movement of the patient's teeth, or a movement rate of the patient's teeth.

The apparatuses and methods described herein may include transmitting (e.g., wirelessly transmitting) one or more of the sensor and/or biosensor data or the processed sensor data to a remote device.

Figures 1A, 1B, 1C, 1D:
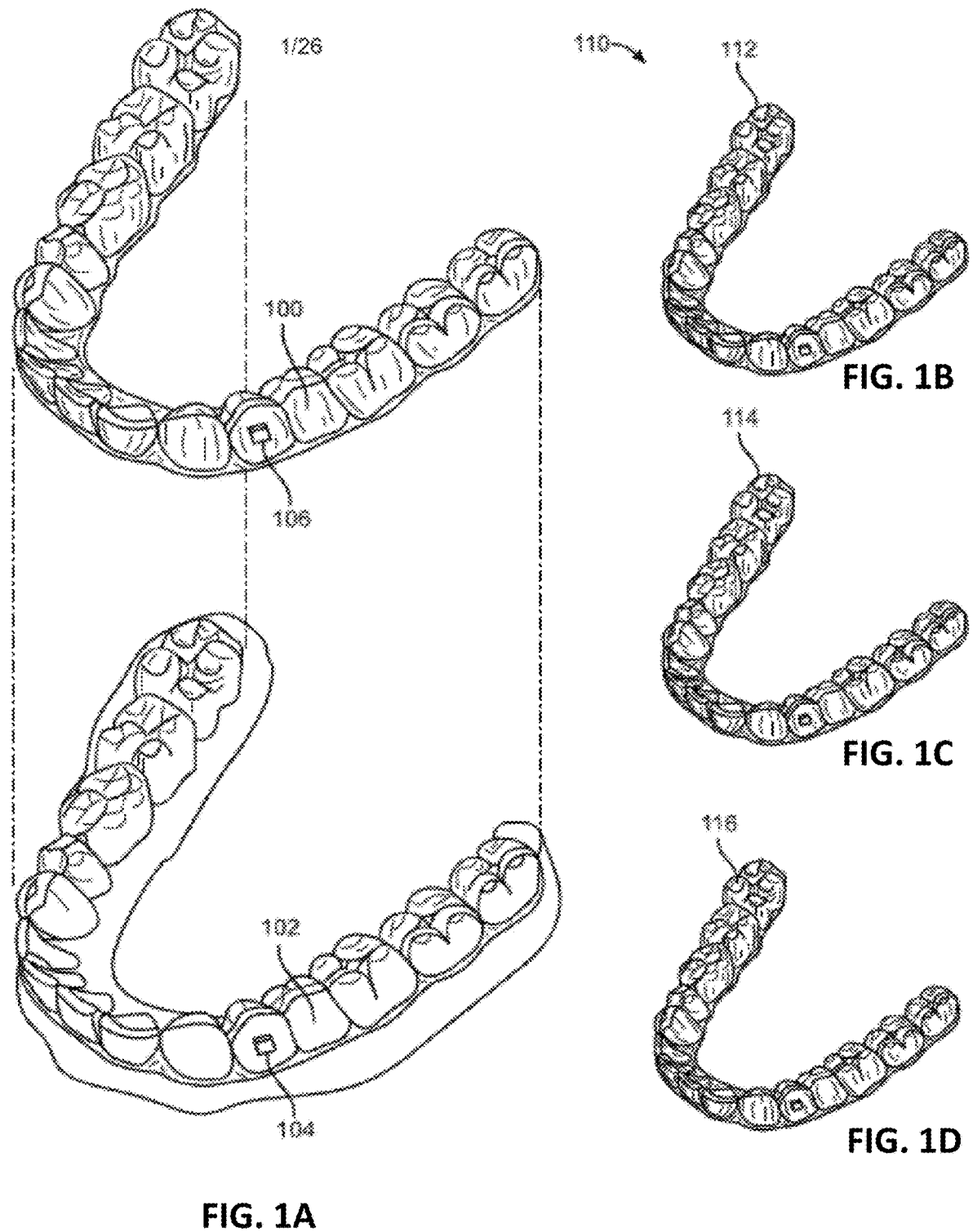
FIG. 1A illustrates a removable orthodontic device (e.g., a tooth repositioning appliance, or aligner), configured as a shell having cavities for fitting over teeth.
FIGS. 1B-1D illustrate a series of removable orthodontic devices (configured as a tooth repositioning system) that may be worn over a subject's teeth to reposition them. Any of these removable orthodontic devices may be configured as described herein to include or operate in conjunction with the biosensors and systems including biosensors as described herein.

As mentioned above, the methods and apparatuses described herein can be used in combination with various types of orthodontic appliances. For example, appliances may have teeth-receiving cavities that receive and/or reposition teeth, e.g., via application of force due to appliance resiliency, are illustrated in FIGS. 1A and 1B-1D. FIG. 1A illustrates an exemplary tooth repositioning appliance or aligner 100 that can be worn by a patient in order to achieve an incremental repositioning of individual teeth 102 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

The methods and apparatuses described herein may be used with any appliance that receives teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth.

As used herein, a dental appliance may include an aligner, such as those utilized in the Invisalign® System, which are described in numerous patents and patent applications assigned to Align Technology, Inc., including, for example, in U.S. Pat. Nos. 6,450,807, and 5,975,893, as well as on the company's website, which is accessible on the World Wide Web (see, e.g., the url "invisalign.com"). In this specification, the use of the terms "orthodontic aligner", "aligner", or "dental aligner" may be synonymous with the use of the terms "appliance" and "dental appliance" in terms of dental applications. For purposes of clarity, embodiments are hereinafter described within the context of the use and application of appliances, and more specifically "dental appliances."

Examples of tooth-mounted attachments suitable for use with orthodontic appliances are also described in patents and patent applications assigned to Align Technology, Inc., including, for example, U.S. Pat. Nos. 6,309,215 and 6,830,450.

FIGS. 1B-1D illustrate a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The orthodontic appliances described herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Orthodontic appliances, such as the appliance illustrated in FIG. 1A, may impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

Figure 2A:
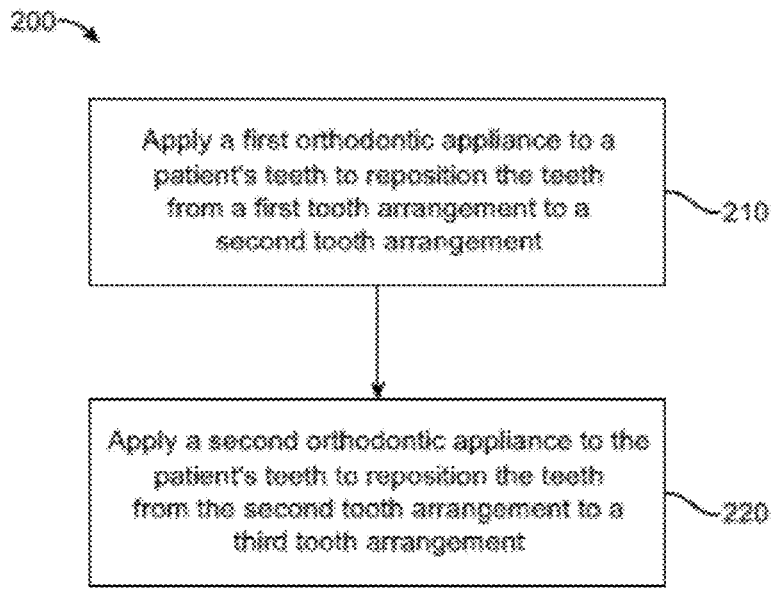
FIG. 2A illustrates a method of orthodontic treatment using a plurality of removable orthodontic devices (e.g., a series of appliances) such as those shown in FIGS. 1B-1D. As mentioned, this method may be modified by using feedback from the one or more biosensors (biosensor systems) as described herein.

FIG. 2 illustrates a method 200 of orthodontic treatment using a plurality of appliances, in accordance with embodiments. The method 200 can be practiced using any of the appliances or appliance sets described herein. In step 210, a first orthodontic appliance is applied to a patient's teeth in order to reposition the teeth from a first tooth arrangement to a second tooth arrangement. In step 220, a second orthodontic appliance is applied to the patient's teeth in order to reposition the teeth from the second tooth arrangement to a third tooth arrangement. The method 200 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 2B:
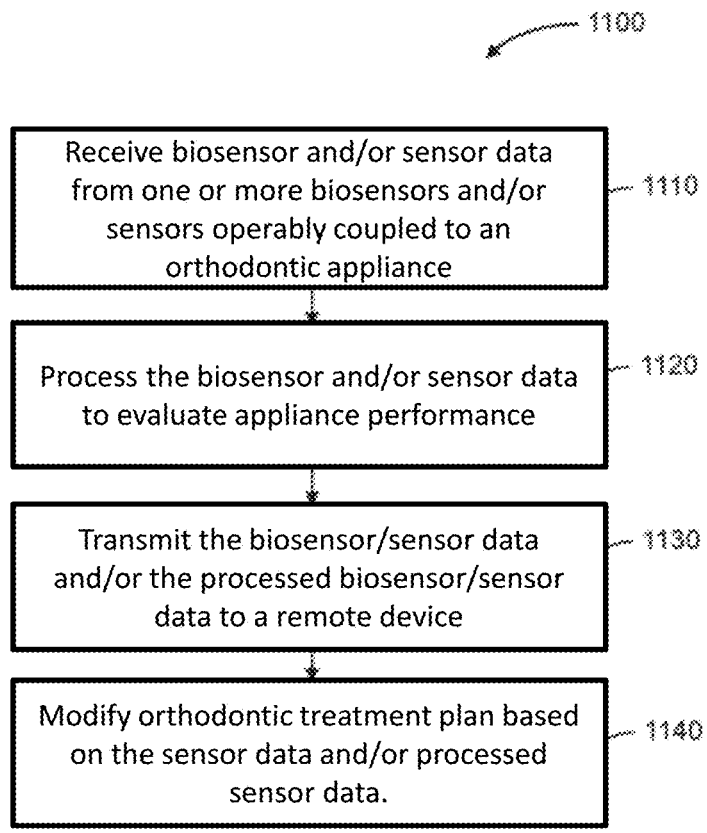
FIG. 2B schematically illustrates a method for monitoring performance of an orthodontic appliance for repositioning a patient's teeth.

FIG. 2B illustrates a method 1100 for monitoring performance of an orthodontic appliance for repositioning a patient's teeth using a biosensor and/or sensor. The method 1100 can be performed using any embodiment of the apparatuses described herein. Some or all of the steps may be performed using a processor of a monitoring device operably coupled to an orthodontic appliance. Alternatively or in combination, some or all of the steps can be performed by a processor of a device external to the patient's intraoral cavity, e.g., a separate computing device or system. As used herein, a monitoring device may refer to the electronics system (subsystem) and may optionally include the one or more biosensors and/or sensors, and may include a housing or case, covering the electronics, power supply, etc.

In step 1110, biosensor and/or sensor data is received from one or more biosensors (and/or sensors) operably coupled to an orthodontic appliance. The one or more biosensors can include any of the biosensor types described herein, including bio sensors testing saliva and/or GCF.

The orthodontic appliance can be worn by the patient as part of a treatment plan for incrementally repositioning the patient's teeth. The orthodontic appliance may include teeth-receiving cavities shaped to reposition one or more teeth according to a prescribed treatment plan, and the biosensor(s) can be physically integrated with (e.g., coupled to, embedded in, formed with, etc.) the orthodontic appliance at locations adjacent to or near the teeth to be repositioned. The bio sensor data can be related to the repositioning of the patient's teeth by the orthodontic appliance. For example, the biosensor data can provide information regarding movements (e.g., rotational, translational) of one or more teeth. As another example, the biosensor data can provide information regarding the interaction between the orthodontic appliance and the patient's teeth or attachment devices mounted thereto. The biosensor data may be generated and logged continuously. Alternatively, in order to reduce power consumption, the biosensor data can be obtained at predetermined time intervals, such as once every 15 minutes, 30 minutes, 1 hour, 2 hours, 5 hours, 12 hours, or 24 hours. The timing for biosensor and/or sensor data collection may vary based on the expected tooth movements to be produced by the orthodontic appliance. For example, in some embodiments, tooth tipping is expected to occur relatively rapidly after the patient starts wearing the appliance, such that monitoring for tooth tipping is performed during the first 12 hours of appliance usage.

In step 1120, the biosensor and/or sensor data is processed in order to evaluate the performance of the orthodontic appliance in repositioning the patient's teeth. For example, the biosensor data can include confirmation that the appliance has triggered remodeling of teeth within a predetermined amount, and the processing step can involve determining whether the analyte indicating remodeling is within a targeted range of values, e.g., for repositioning the teeth. Alternatively or in combination, the biosensor and/or sensor data can include measurement of changes in the spatial disposition (e.g., position and/or orientation) of one or more teeth, and the processing step can involve determining whether the changes in spatial disposition correspond to planned movements for the patient's teeth. Optionally, the processing step can involve associating the biosensor data with a timestamp representing when the data was obtained such that appliance performance information can be measured over time.

The processed biosensor data can include appliance performance information, e.g., whether the force(s), pressure(s), and/or tooth movement(s) produced by the appliance correlate well with the expected values for the planned orthodontic treatment. The expected values for a planned treatment may be determined by computer simulation. For example, an orthodontic appliance can be considered to be performing satisfactorily if: (1) the measured force and/or pressure values lie within the expected range for those values, or is within 70% of a targeted value; (2) the pattern of force and/or pressure application on the teeth matches, or is similar to, the planned pattern for force and/or pressure application; (3) the amount of tooth movement achieved is within 70% of the planned movement; (4) the direction of tooth movement matches, or is similar to, the planned direction of tooth movement; or combinations thereof. An orthodontic appliance can be considered to be performing unsatisfactorily if: (1) the measured force and/or pressure values lie outside the expected range for those values or is more than 30% away from a targeted value; (2) the pattern of force and/or pressure application on the teeth differs from the planned pattern for force and/or pressure application; (3) the amount of tooth movement achieved is more than 30% away from the planned movement; (4) the direction of tooth movement is different to the planned direction of tooth movement; or combinations thereof.

In step 1130, the biosensor data generated in step 1110 and/or the processed biosensor data generated in step 1120 are optionally transmitted to a remote device. The remote device can be a mobile device (e.g., smartphone), personal computer, laptop, tablet, wearable device, cloud computing server, or the like. Step 1130 can be performed using wireless or wired communication methods, as desired. Step 1130 can be performed automatically (e.g., at predetermined time intervals) or in response to instructions received from the remote device (e.g., a command to transmit the biosensor and/or sensor data and/or appliance usage).

In step 1140, the orthodontic treatment plan prescribed to the patient is optionally modified based on the biosensor and/or sensor data generated in step 1110 and/or the processed biosensor data generated in step 1120. The modification step can be performed by a processor external to the patient's intraoral cavity, such as a remote device as in step 1130. Modifying the treatment plan can involve modifying a planned intermediate or final arrangement of the patient's teeth, modifying the teeth-receiving cavity geometries of an orthodontic appliance corresponding to a planned intermediate or final tooth arrangement, modifying the timing for wearing one or more appliances, modifying the order for wearing a series of appliances, or a combination thereof. For example, if the appliance performance information indicates that the tooth repositioning achieved by the orthodontic appliance is not satisfactory and the teeth are off-track, the treatment plan can be modified in order to move the patient's teeth back on track (e.g., mid-course correction). As another example, if the appliance performance information indicates that the appliance is not producing the desired force and/or pressure pattern on the teeth, the geometries of subsequent appliances can be adjusted accordingly to provide more accurate force and/or pressure application. By using the appliance performance information as feedback, these methods and apparatuses allow for adaptive, closed-loop orthodontic treatment based on the actual response of the patient's teeth to treatment.

The monitoring devices described herein can be physically integrated into an orthodontic appliance in a variety of ways. In some embodiments, the monitoring device is integrated into the appliance during or after fabrication of the appliance. For example, the monitoring device can be attached to an appliance using adhesives, fasteners, a latching mechanism, or a combination thereof after the appliance has been fabricated. Optionally, the appliance can be formed with complementary features or structures (e.g., recesses, receptacles, guides, apertures, etc.) shaped to receive and accommodate the monitoring device or components thereof.

A monitoring device may be coupled to the appliance as a prefabricated unit during or after fabrication of the appliance, such as by being inserted and sealed into a receptacle in the appliance, attached to an appliance (e.g., by a latching mechanism, adhesive, fastener). Alternatively, the monitoring device can be assembled in situ on the appliance during or after appliance fabrication. For instance, in embodiments where the appliance is manufactured by direct fabrication (e.g., 3D printing), the monitoring device can be printed simultaneously with the appliance, inserted into the appliance during fabrication, or after assembled the appliance has been fabricated. Optionally, some of the monitoring device components may be prefabricated and other components may be assembled in situ. It shall be appreciated that the various fabrication methods described herein can be combined in various ways in order to produce an appliance with integrated monitoring device components.

An orthodontic appliance can be operably coupled to a monitoring device configured to provide data related to tooth repositioning and/or the interaction between the appliance and the patient's teeth (e.g., contact between the appliance and the teeth, the amount of force and/or pressure applied by the appliance to the teeth, distribution of force and/or pressure on the teeth, etc.). Such data can be used to evaluate the performance of the orthodontic appliance for repositioning the patient's teeth. For instance, appliance performance information as described herein can include information regarding whether the force(s), pressure(s), and/or tooth movement(s) produced by an orthodontic appliance correlate with the expected values for the planned orthodontic treatment.

The monitoring devices described herein can be designed for use in the patient's intraoral cavity. For example, the dimensions of a monitoring device may be limited in order to avoid patient discomfort and/or facilitate integration into an orthodontic appliance as discussed below. In some embodiments, a monitoring device has a height or thickness less than or equal to about 1.5 mm, or less than or equal to about 2 mm. In some embodiments, a monitoring device has a length or width less than or equal to about 4 mm, or less than or equal to about 5 mm. The shape of the monitoring device can be varied as desired, e.g., circular, ellipsoidal, triangular, square, rectangular, etc. For instance, in some embodiments, a monitoring device can have a circular shape with a diameter less than or equal to about 5 mm.

A relatively thin and flexible monitoring device can be used to provide a larger surface area while reducing patient discomfort. In some embodiments, the monitoring devices herein are sized to conform to a surface of a tooth crown (e.g., a buccal, lingual, and/or occlusal surface of a tooth crown). For example, a monitoring device having dimensions of about 10 mm by about 5 mm can be used to cover a buccal surface of a molar crown. As another example, a monitoring device having dimensions of about 10 mm by about 20 mm can be used to cover the buccal, occlusal, and lingual surfaces of a tooth crown. A monitoring device can be in contact with a crown of a single tooth, or with crowns of a plurality of teeth, as desired.

The monitoring device dimensions (e.g., volume, weight) can be designed in order to reduce patient discomfort. For instance, the weight of a monitoring device can be selected not to exceed a level that would exert undesirable forces on the underlying teeth. A monitoring device may be used primarily for research and characterization purposes, rather than for patient treatment, and thus may not be subject to size constraints for reducing patient discomfort. For example, in embodiments where the monitoring device is used outside the intraoral cavity (e.g., benchtop testing of aligner performance), the size of the monitoring device can be relatively large compared to devices designed for intraoral use.

As discussed above, FIG. 3 schematically illustrates an example of an apparatus (e.g., a monitoring device 300 portion of an apparatus), that may be used or include an orthodontic appliance (not shown). The monitoring device 300 can be used in combination with any embodiment of the systems and devices described herein, and the components of the monitoring device 300 are equally applicable to any other embodiment of the apparatuses, including monitoring devices, described herein. The monitoring device 300 can be implemented as an application-specific integrated circuit (ASIC) including one or more of the following components: a processor 302, a memory 304, one or more biosensors and/or sensors 306, a clock 308, a communication unit 310, an antenna 312, a power management unit 314, or a power source 316. The processor 302 (e.g., a central processing unit (CPU), microprocessor, field programmable gate array (FPGA), logic or state machine circuit, etc.), also referred to herein as a controller, can be configured to perform the various methods described herein. The memory 304 encompasses various types of memory known to those of skill in the art, such as RAM (e.g., SRAM, DRAM), ROM (EPROM, PROM, MROM), or hybrid memory (e.g., flash, NVRAM, EEPROM), and the like. The memory 304 can be used to store instructions executable by the processor 302 to perform the methods provided herein. Additionally, the memory can be used to store biosensor/sensor data obtained by the biosensor(s)/sensors 306, as discussed in greater detail below.

The monitoring device 300 can include any number of biosensors 306 and/or sensor 306', such as one, two, three, four, five, or more biosensors. In some embodiments, the use of multiple biosensors provides redundancy to increase the accuracy and reliability of the resultant data. Some or all of the biosensors 306 can be of the same type. Some or all of the biosensors 306 can be of different types. Examples of biosensor types suitable for use in the monitoring devices described herein are provided below. Examples of additional sensors may include: touch or tactile sensors (e.g., capacitive, resistive), proximity sensors, movement sensors (e.g., electromagnetic field sensors), force sensors (e.g., force-sensitive resistive or capacitive materials), pressure sensors (e.g., pressure-sensitive resistive or capacitive materials), strain gauges (e.g., resistive- or MEMS-based), electrical sensors, or combinations thereof.

A biosensor 306 can be operably coupled to and/or located at any portion of an orthodontic appliance, such as at or near a distal portion, a mesial portion, a buccal portion, a lingual portion, a gingival portion, an occlusal portion, or a combination thereof. A bio sensor 306 can be positioned near a tissue of interest when the appliance is worn in the patient's mouth, such as near or adjacent the teeth, gingiva, palate, lips, tongue, cheeks, airway, or a combination thereof. For example, when the appliance is worn, the biosensor(s) 306 can cover a single tooth, or a portion of a single tooth. Alternatively, the biosensor(s) 306 can cover multiple teeth or portions thereof. In embodiments where multiple biosensors 306 are used, some or all of the monitoring devices can be located at different portions of the appliance and/or intraoral cavity. Alternatively, some or all of the biosensors 306 can be located at the same portion of the appliance and/or intraoral cavity.

An analog-to-digital converter (ADC) (not shown) can be used to convert analog biosensor and/or sensor data into digital format, if desired. The processor 302 can process the data obtained by the biosensor(s) 306 in order to determine appliance usage and/or patient compliance, as described herein. The biosensor data and/or processing results can be stored in the memory 304. Optionally, the stored data can be associated with a timestamp generated by the clock 308 (e.g., a real-time clock or counter).

In some embodiments, the monitoring device 300 includes a communication unit 310 configured to transmit the data stored in the memory (e.g., biosensor data and/or processing results) to a remote device. The communication unit 310 can utilize any suitable communication method, such as wired or wireless communication methods (e.g., RFID, near-field communication, Bluetooth, ZigBee, infrared, etc.). The communication unit 310 can include a transmitter for transmitting data to the remote device and an antenna 312. Optionally, the communication unit 310 includes a receiver for receiving data from the remote device. In some embodiments, the communication channel utilized by the communication unit 310 can also be used to power the device 300, e.g., during data transfer or if the device 300 is used passively.

The remote device can be any computing device or system, such as a mobile device (e.g., smartphone), personal computer, laptop, tablet, wearable device, etc. Optionally, the remote device can be a part of or connected to a cloud computing system ("in the cloud"). The remote device can be associated with the patient, the treating practitioner, medical practitioners, researchers, etc. In some embodiments, the remote device is configured to process and analyze the data from the monitoring device 300, e.g., in order to assess appliance performance, for research purposes, and the like.

The monitoring device 300 can be powered by a power source 316, such as a battery. In some embodiments, the power source 316 is a printed and/or flexible battery, such as a zinc-carbon flexible battery, a zinc-manganese dioxide printed flexible battery, or a solid-state thin film lithium phosphorus oxynitride battery. The use of printed and/or flexible batteries can be advantageous for reducing the overall size of the monitoring device 300 and avoiding patient discomfort. For example, printed batteries can be fabricated in a wide variety of shapes and can be stacked to make three-dimensional structures, e.g., to conform the appliance and/or teeth geometries. Likewise, flexible batteries can be shaped to lie flush with the surfaces of the appliance and/or teeth. Alternatively or in combination, other types of batteries can be used, such as supercapacitors. In some embodiments, the power source 316 can utilize lower power energy harvesting methods (e.g., thermodynamic, electrodynamic, piezoelectric) in order to generate power for the monitoring device 300. Optionally, the power source 316 can be rechargeable, for example, using via inductive or wireless methods. In some embodiments, the patient can recharge the power source 316 when the appliance is not use. For example, the patient can remove the orthodontic appliance when brushing the teeth and place the appliance on an inductive power hub to recharge the power source 316.

Optionally, the apparatus can include a power management unit 314 connected to the power source 316. The power management unit 314 can be configured to control when the apparatus is active (e.g., using power from the power source 316) and when the apparatus inactive (e.g., not using power from the power source 316). In some embodiments, the monitoring device 300 is only active during certain times so as to lower power consumption and reduce the size of the power source 316, thus allowing for a smaller monitoring device 300

The apparatus may also include an activation mechanism (not shown) for controlling when the monitoring device (e.g., control circuitry) 300 is active (e.g., powered on, monitoring appliance usage) and when the monitoring device 300 is dormant (e.g., powered off, not monitoring appliance usage). The activation mechanism can be provided as a discrete component of the monitoring device 300, or can be implemented by the processor 302, the power management unit 314, or a combination thereof. The activation mechanism can be used to reduce the amount of power used by the monitoring device 300, e.g., by inactivating the device 300 when not in use, which can be beneficial for reducing the size of the power supply 316 and thus the overall device size.

In some embodiments, the monitoring device 300 is dormant before being delivered to the patient (e.g., during storage, shipment, etc.) and is activated only when ready for use. This approach can be beneficial in conserving power expenditure. For example, the components of the monitoring device 300 can be electrically coupled to the power source 316 at assembly, but may be in a dormant state until activated, e.g., by an external device such as a mobile device, personal computer, laptop, tablet, wearable device, power hub etc. The external device can transmit a signal to the monitoring device 300 that causes the activation mechanism to activate the monitoring device 300. As another example, the activation mechanism can include a switch (e.g., mechanical, electronic, optical, magnetic, etc.), such that the power source 316 is not electrically coupled to the other components of the monitoring device 300 until the switch is triggered. For example, the switch may be a reed switch or other magnetic sensor that is held open by a magnet. The magnet can be removably attached to the monitoring device 300, or may be integrated into the packaging for the device 300 or appliance, for example. When the monitoring device is separated from the magnet (e.g., by removing the magnet or removing the device and appliance from the packaging), the switch closes and connects the power source 316, as illustrate in FIG. 4B. As another example, the monitoring device 300 can include a mechanical switch such as a push button that is manually actuated in order to connect the power source 316. In some embodiments, the activation mechanism includes a latching function that locks the switch upon the first actuation to maintain connectivity with the power source so as to maintain activation of the monitoring device 300. Optionally, the switch for the activation mechanism can be activated by a component in the patient's intraoral cavity (e.g., a magnet coupled to a patient's tooth), such that the monitoring device 300 is active only when the appliance is worn by the patient, and is inactive when the appliance is removed from the patient's mouth. Alternatively or in combination, the switch can be activated by other types of signals, such as an optical signal.

FIG. 4B illustrates a monitoring device 400 with an activation mechanism. The monitoring device 400, as with all other monitoring devices described herein, can be similar to the monitoring device 300, and can include some or all of the components described herein with respect to the monitoring device 300. The device 400 is coupled to an orthodontic appliance 402 (e.g., via an encapsulating material 404). The device 400 can include an activation mechanism 403 including a magnetic switch. Prior to use, the device 400 can be removably coupled to a magnet 406 (e.g., using tape 408), and the magnet 406 can hold the magnetic switch in an open position such that the device 400 is inactive. When the appliance 402 is ready for use, the user can remove the magnet 406, thus closing the magnetic switch and connecting the components of the monitoring device 400 to a power source.

The orthodontic appliances and monitoring devices can be configured in many different ways. In some embodiments, an orthodontic appliance may be operably coupled to a single monitoring device. Alternatively, the orthodontic appliance can be operably coupled to a plurality of monitoring devices, such as at least two, three, four, five, or more monitoring devices. Some or all of the monitoring devices may be of the same type (e.g., collect the same type of data). Alternatively, some or all of the monitoring devices may be of different types (e.g., collect different types of data). Any of the embodiments of monitoring devices described herein can be used in combination with other embodiments in a single orthodontic appliance.

A monitoring device can be located at any portion of the appliance, such as at or near a distal portion, a mesial portion, a buccal portion, a lingual portion, a gingival portion, an occlusal portion, or a combination thereof. The monitoring device can be positioned near a tissue of interest when the appliance is worn in the patient's mouth, such as near or adjacent the teeth, gingiva, palate, lips, tongue, cheeks, airway, or a combination thereof. For example, when the appliance is worn, the monitoring device can cover a single tooth, or a portion of a single tooth. Alternatively, the monitoring device can cover multiple teeth or portions thereof. In embodiments where multiple monitoring devices are used, some or all of the monitoring devices can be located at different portions of the appliance. Alternatively, some or all of the monitoring devices can be located at the same portion of the appliance.

A monitoring device can be operably coupled to the orthodontic appliance in a variety of ways. For example, the monitoring device can be physically integrated with the orthodontic appliance by coupling the monitoring device to a portion of the appliance (e.g., using adhesives, fasteners, latching, laminating, molding, etc.). The coupling may be a releasable coupling allowing for removal of the monitoring device from the appliance, or may be a permanent coupling in which the monitoring device is permanently affixed to the appliance. Alternatively or in combination, the monitoring device can be physically integrated with the orthodontic appliance by encapsulating, embedding, printing, or otherwise forming the monitoring device with the appliance. In some embodiments, the appliance includes a shell shaped to receive the patient's teeth, and the monitoring device is physically integrated with the shell. The monitoring device can be located on an inner surface of the shell (e.g., the surface adjacent to the received teeth), an outer surface of the shell (e.g., the surface away from the received teeth), or within a wall of the shell. Optionally, as discussed further herein, the shell can include a receptacle shaped to receive the monitoring device. Exemplary methods for fabricating an appliance with a physically integrated monitoring device (e.g., by incorporating some or all of the components of the monitoring device during direct fabrication of the appliance) are described in further detail herein.

FIGS. 5A and 5B illustrate an example of an apparatus including an orthodontic appliance 500 having an integrated monitoring device (control circuitry) 502 and biosensor. In this example, the appliance 500 includes a shell 504 having one or more (e.g., a plurality of) teeth-receiving cavities, and the monitoring device 502 is coupled to an outer, buccal surface of the shell 504 adjacent a tooth receiving cavity 506. In the depicted embodiment, the monitoring device 502 is coupled to a tooth receiving cavity 506 for a molar. It shall be appreciated that in alternative embodiments, the monitoring device 502 can be coupled to other portions of the shell 504, such as an inner surface, a lingual surface, an occlusal surface, one or more tooth receiving cavities for other types of teeth (e.g., incisor, canine, premolar), etc. The monitoring device 502 can be shaped to conform to the geometry of the corresponding appliance portion (e.g., the wall of the cavity 306) so as to provide a lower surface profile and reduce patient discomfort. In some embodiments, the appliance 500 includes a receptacle 508 formed on the outer surface of the shell 504 and the monitoring device 502 is positioned within the receptacle. Exemplary methods for forming an appliance with a receptacle 508 and integrated monitoring device 502 are described in detail below.

The monitoring device 502 can include any of the components previously described herein with respect to the monitoring device 300 of FIG. 3. For example, the monitoring device 502 can include a biosensor 510 and/or sensor, a power source 512 (e.g., a battery), and/or a communication unit 514 (e.g., a wireless antenna). The arrangement of the components of the monitoring device 502 can be varied as desired. In some embodiments, the biosensor 551 is located adjacent to the tooth receiving cavity 506. A gap can be formed in the shell 504 adjacent to the biosensor/sensor 510 so as to permit direct access to the received tooth. The communication unit 514 (or a component thereof, such as an antenna) can be located adjacent to or on the outer surface of the receptacle 408 so as to facilitate data transmission.

Some of the components of a monitoring device may be packaged and provided separately from other components of the device. For example, a monitoring device can include one or more components that are physically integrated with a first orthodontic appliance and one or more components that are physically integrated with a second orthodontic appliance. The first and second orthodontic appliances can be worn on opposing jaws, for example. Any of the components of a monitoring device (e.g., components of the device 300 of FIG. 3) can be located on an appliance for the upper jaw, an appliance for the lower jaw, or a combination thereof. In some embodiments, it is beneficial to distribute the components of the monitoring device across multiple appliances in order to accommodate space limitations, accommodate power limitations, and/or improve sensing, for example. Additionally, some of the components of a monitoring device can serve as a substrate for other components (e.g., a battery serves as a substrate to an antenna).

Alternatively or in combination, other types of bio sensor/sensor can be used to indirectly measure the forces and/or pressures applied to the teeth by an appliance. For example, in some embodiments, the application of force and/or pressure to a patient's teeth produces electrical currents (for example, via the piezoelectric effect) in structures of the mouth. Compression of bone and collagen may result in movement of electrons in the crystal lattice, and application of force on the teeth can result in a short piezoelectric effect on the alveolar bone, which may be detected by appropriate receiving sensors such as electrodes. Electrical signals produced by alveolar and periodontal ligaments (PDL) when under load can stimulate changes in bone metabolism. This piezoelectric effect can be measured to determine when a tooth is loaded or overloaded by an appliance. Electrical sensors such as electrodes may also be used to detect these electrical signals, for example, by monitoring changes in voltage.

Alternatively or in combination, the monitoring devices herein can include one or more tactile sensors that respond to direct contact with the patient's teeth. The tactile sensors described herein can be capacitive sensors, resistive sensors, inductive sensors, or piezoelectric sensors, for example. For example, the tactile sensor can be a piezoelectric sensor including one or more materials that exhibit piezoelectric properties, such as quartz, ceramics, or polymers (e.g., polyvinylidene fluoride (PVDF)).

In some embodiments, a biosensor can be a sensor array that capable of detecting contact over a two-dimensional surface area. Optionally, a tactile sensor can be provided as a clear, thermoformable screen or film capable of conforming to the shape of the appliance. Some types of tactile sensors may only be capable of providing contact data (e.g., binary data indicating the presence or absence of direct contact), while other types of tactile sensors may also be capable of providing other types of data in addition to contact data (e.g., resistive tactile sensors capable of providing force and/or pressure data).

A monitoring device can include a single biosensor, or a plurality of biosensors and/or other sensors can be positioned at any location in the appliance, such on an inner surface, an outer surface, a buccal surface, a lingual surface, an occlusal surface, a mesial portion, a distal portion, a gingival portion, or a combination thereof. In embodiments where the orthodontic appliance includes a shell with a teeth-receiving cavity, the biosensors/sensors can be positioned on the inner surfaces of the teeth-receiving cavities. Optionally, at least some biosensors can be located on an outer surface of the appliance, such as an occlusal surface in order to detect contact between the upper and lower teeth The biosensors can be positioned to be near certain teeth when the appliance is worn, e.g., near teeth to be repositioned and/or at locations where the appliance is expected to exert force on the teeth. For example, tactile sensors can be located at or near the buccal, lingual, and/or occlusal surfaces of a tooth to be repositioned so as to provide a map of contact points over the tooth crown. In some embodiments, the monitoring device is configured to obtain data from buccal, lingual, and occlusal sensors in a predetermined order and at a desired frequency in order to provide a contact map over the buccal, lingual, and occlusal surfaces. Alternatively or in combination, if the appliance is shaped to engage an attachment device mounted on a tooth, a tactile sensor can be located at or near the location of engagement between the appliance and the attachment device.

Alternatively or in combination, an apparatus as described herein can include one or more movement sensors for measuring the movements (e.g., translational and/or rotational movements) of one or more teeth. For example, a movement sensor can be used track the movements of one or more teeth relative to the underlying jaw (e.g., mandible or maxilla). As another example, a movement sensor can be used to track the movements of a first set of one or more teeth relative to a second set of one or more teeth, such as when tracking the movements of opposite sides of a single arch during arch or palate expansion. Optionally, a movement sensor can be used to track movements of the upper and lower arches relative to each other, such as when correcting the relative positioning of the arches in order to treat overbite or underbite. Various types of movement sensors can be used. In some embodiments, a movement sensor includes an electromagnetic field generator (e.g., an electromagnetic coil, generator antenna) integrated into an orthodontic appliance or an attachment device mounted on a patient's tooth. The generator can be configured to generate an electromagnetic field (e.g., electric field, magnetic field, or combination thereof) within the intraoral cavity. The movement sensor can also include one or more electromagnetic targets (e.g., a cylindrical or flat coil, magnet, etc.) integrated into an orthodontic appliance (e.g., the same appliance as the generator, a different appliance worn on the opposite jaw, or a combination thereof). The electromagnetic targets can be positioned in the appliance at or near locations where tooth movement is expected to occur (e.g., coupled to teeth-receiving cavities of teeth to be repositioned), such that the movements of the teeth produce corresponding movements of the electromagnetic targets. Alternatively or in combination, the monitoring device can include one or more electromagnetic targets integrated into an attachment device coupled to the patient's teeth, such that the movements of the teeth and associated targets are directly correlated.

Alternatively or in combination, any of the apparatuses described herein can include one or more electrical sensors (e.g., electrodes) to measure tooth surface charges, as mentioned above. Alveolar bone remodeling during orthodontic tooth movement may be regulated by stress-induced bioelectric potentials on the tooth surface. For example, a force applied to the labial surface of the lower incisor can displace the tooth in its socket, deforming the alveolar bone convexly towards the root at the leading edge, and producing concavity towards the root at the trailing edge. In some embodiments, concave bone surfaces characterized by osteoblastic activity are electronegative, and convex bone surfaces characterized by osteoclastic activity are electropositive or electrically neutral. Accordingly, the monitoring device can measure the electrical charges on the tooth surface in order to determine the tooth movement rate and/or direction.

Alternatively or in combination, any of the apparatuses described herein can include one or more conductivity sensors configured to measure the conductivity of fluids (e.g., saliva) in the surrounding environment. In some embodiments, bone remodeling during orthodontic tooth movement causes changes in saliva content, and these changes can be measured based on the ionic charge of the minerals in the saliva. Examples of minerals that may influence the conductivity of saliva include but are not limited to $NH4+$, $Ca2+$, $PO43"$, $HCO3-$, and $F"$.

In general, the apparatuses described herein may include miniaturized and integrated electronic components (e.g., battery, antenna, controller, wireless communication circuitry, etc.) as part of an embedded biosensing apparatus. In some variations, the biosensor may include detection of one or more types of biomarker in saliva, including those in Table 1, above. For example, a Potentiostat with a screen-printed electrode and a modified enzyme layer may be used to detect a salivary biomarker (e.g., 14-3-3 protein σ (Stratifin), uric acid, etc.). A working electrode (biotransducer) may be chemically modified by crosslinking to an enzyme. An antifouling layer may be included to prevent interference effects and biofouling.

The apparatus may include electrodes for differential C2D (e.g., common to differential) measurements and input channels for A2D (analog to digital) voltage measurements. One or more electrodes may be layered with an enzyme-membrane to achieve different configurations of working electrodes. Additional sensors and/or biosensors may be used, including temperature measurements. For example, one or more sensors can provide proximity data, which can augment biomarker detection.

In any of these apparatuses and methods described herein, compliance data may be determined from the biosensor/sensor data, and this information may also be used to augment, control, and/or interpret the biosensor information. For example, compliance data may be estimated by determining a working state of the apparatus from proximity data (e.g., power states for "In-mouth" and "out-of-mouth" conditions). Temperature sensing may also be used to augment biomarker data, e.g., by correlating temperature and biomarker data, which may provide more specific physiological monitoring.

As discussed above, examples of biomarkers that may be detected by the apparatuses and methods herein may include salivary biomarkers such as sRANKL, OPG, which may be correlated to different phases of orthodontic tooth movement (e.g., https://www.ncbi.nlm.nih.gov/pubmed/23273364). Other salivary markers include S100-A9, immunoglobulin J chain, Ig alpha-1 chain C region, CRISP-3, which may indicate inflammation and bone resorption (see, e.g., https://www.ncbi.nlm.nih.gov/pmc/articles/PMC3417200/).

Examples of gingival crevicular fluid biomarkers, e.g., inflammatory fluid accessible in in the gingival margin, may include prostaglandin E2 (which may indicate bone resorption), Substance P (neuropeptide) (which may indicate bone resorption), epidermal growth factor (which may indicate bone resorption), transforming growth factor (which may indicate bone remodeling), RankL (which may indicate stimulation of osteoclsatic differentiation), Granulocyet macrophage colony stimulation factor (which may indicate bone turnover), α2 microglobulin-enhance of IGF 1, Interleukin 1β, 2, 6, 8 (which may indicate bone remodeling), Myeloperoxidase (and enzyme involved in PMN inflammation). Other gingival crevicular fluid biomarkers may include glycosaminoglycans (GAGs or mucopolysaccharides), and may indicate paradental remodeling, such as hyaluronic acid (a type of GAG or mucopolysaccharide, indicator of breakdown of gingival tissue), and Chondroitin sulfate (another type of GAG, an indicator of breakdown of alveolar bone and PDL).

Also described herein are textile-based sensors. Such sensors may include stretchable conductive ink, and may be used when forming the apparatus (e.g., on an aligner). For example, a textile-based sensor may be co-formed with the apparatus or added to it, or added directly onto the teeth. In some variations the sensor including a conductive "ink" may be screen printed as a trace on a flexible substrate, including fabric substrates or polymeric substrates. The appliance (e.g., aligner) may then be formed specific to the patient, as described above. The flexible substrate with the printed sensor and/or trace may then be applied (or alternatively screened directly) on/over the aligner. Thus, the stretchable conductive ink may be directly applied over the aligner.

Alternatively, as mentioned, a sensor, such as a stretchable sensor, may be bonded directly to the teeth or other intra oral tissue. This may provide better access to GCF or saliva for the biosensor/sensor. Instead of an embedded biosensor on the aligner, the biosensor may be directly bonded to the gingival margin to monitor GCF for certain biomarkers.

Any of the biosensors/sensors described herein may be powered by a flexible fuel cell, such as a stretchable rechargeable battery. Thus, the entire sensing apparatus or sub-system may be flexible and/or may be bonded directly to the tooth. Alternatively or additionally, a sensor (broadly including a biosensor) may be powered and/or augmented by electronics in an appliance (e.g., aligner). For example, the sensor may need to be bonded to the tooth for better monitoring of the physiological signal, but driving electronics may be located on a replaceable aligner (for renewed energy supply, data collection, signal processing, etc.).

FIGS. 6A-6C illustrate an example of an apparatus bonded directly to the subject's teeth. In FIG. 6A, the apparatus includes a stretchable conductive trace that is directly attached to the teeth. In this example, the traces connect nodes A and B to the power supply nodes C and D, which are on the aligner. This configuration may eliminate leakage current from the battery to the components (X) when the aligner is not in the mouth. In one example, the components generically referred to as "X" in FIG. 6A-6C could include electronics which drive a BLE signal every few minutes (e.g., every minute, 2 minutes, 3 minutes, 5 minutes, 10 minutes, 15 minutes, etc., or variable intervals/times). A receiver (e.g., smartphone and/or dedicated receiver) could track the BLE pulses and monitor when the appliance is in the mouth.

In FIG. 6A, the traces 603 shown on the teeth 601 can be used to connect to rigid components on the aligner. Different electronic circuits may be used when the aligner is in the mouth and for when the aligner is outside of the mouth. For example, traces such as those shown above can be used as performance measures for aligners or tooth movements. Nodes 607 can be placed to be at known positions on the aligner and compared with nodes positions on teeth. In some variations a printed potentiometer may be applied to the teeth. As shown in FIG. 6B, before the aligner is worn, the contacts (A, B) or nodes are not connected, to the power (on left, nodes D and C), which may be on the aligner. When the aligner is worn (shown in FIG. 6C), the circuit is completed, as nodes A and D connect and nodes B and C connect by the conductive trace. At a minimum, this completed circuit may be used to indicate compliance, as it will only complete the circuit when the appliance is worn, and worn correctly. Alternatively, additional sensor(s), including one or more biosensor, may also be connected to the traces on the subject's teeth (either on the tooth/teeth, or on the aligner) and activated when the appliance is worn. In some variations, the use of conductive traces on the teeth that may interface with contacts on an aligner may also be used to check the fit of an aligner.

In some variations the traces, such as those shown in FIGS. 6A-6C may be magnetic, which may allow self-healing of the traces, or may also be used for other purposes, including detection (e.g., via a reed switch or hall-effect sensor, etc.) including detection of teeth.

Figure 8:
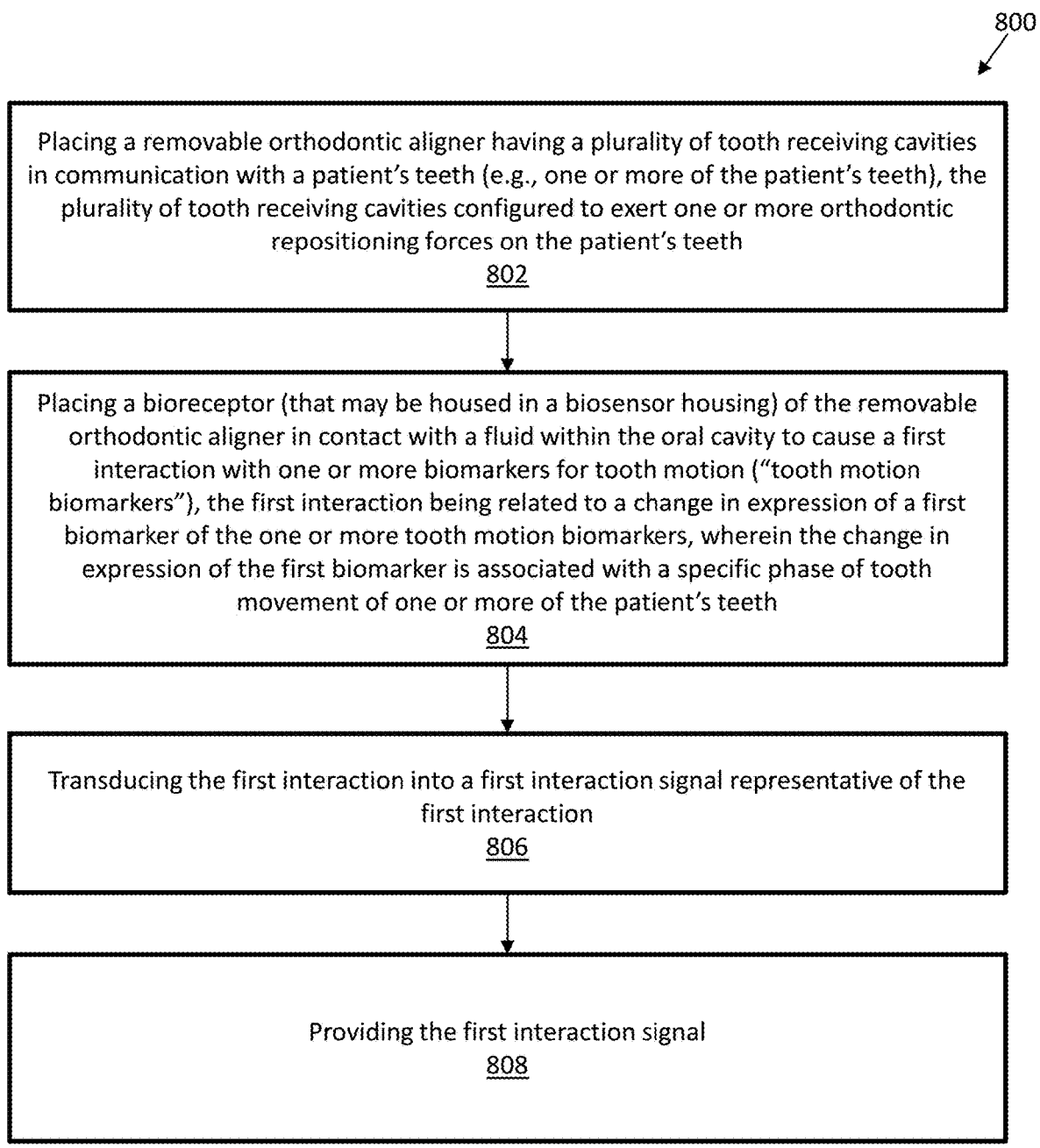
FIG. 8 illustrates an example of a method of operating a removable orthodontic device (e.g., appliance) including a biosensor.

As mentioned above, any of the bio sensor systems and apparatuses (e.g., removable orthodontic devices) described herein may be used to monitor one or more biomarkers from a patient. For example, FIG. 8 schematically illustrates one example of a method of monitoring a biomarker from a patient using a removable orthodontic device, such as an aligner, that includes a biomarker. As mentioned above, as an initial step (not shown) a removable orthodontic device that does not apply substantial force to move the teeth but that includes a bio sensor system may be first worn, and a baseline for the one or more biomarkers collected. In FIG. 8, a removable orthodontic device (e.g., aligner) having a biosensor may be worn by the patient. For example, the removable orthodontic device may have a plurality of tooth receiving cavities that may be placed in communication with a patient's teeth (e.g., one or more of the patient's teeth). The plurality of tooth receiving cavities may be configured to exert one or more orthodontic repositioning forces on the patient's teeth 802.

While the aligner is worn, the bioreceptor (that may be housed in a bio sensor housing) of the removable orthodontic aligner may be placed in contact with a fluid (e.g., saliva, GCF, blood) within the oral cavity, which may cause a first interaction with one or more biomarkers for tooth motion ("tooth motion biomarkers"). The first interaction may be related to a change in expression of a first biomarker of the one or more tooth motion biomarkers, wherein the change in expression of the first biomarker is associated with a specific phase of tooth movement of one or more of the patient's teeth 804. For example, the level of the biomarker compared to a baseline may be indicative of the phase of tooth movement (e.g., initial phase, lag phase, etc.). A threshold or range of sensed values may be used to monitor an effect of the removable orthodontic device on the teeth. For example, the first interaction may be transduced into a first interaction signal representative of the first interaction 806, and this first interaction signal may be provided by the device 808. For example it may be output (transmitted, displayed, stored, etc.).

Figure 9:
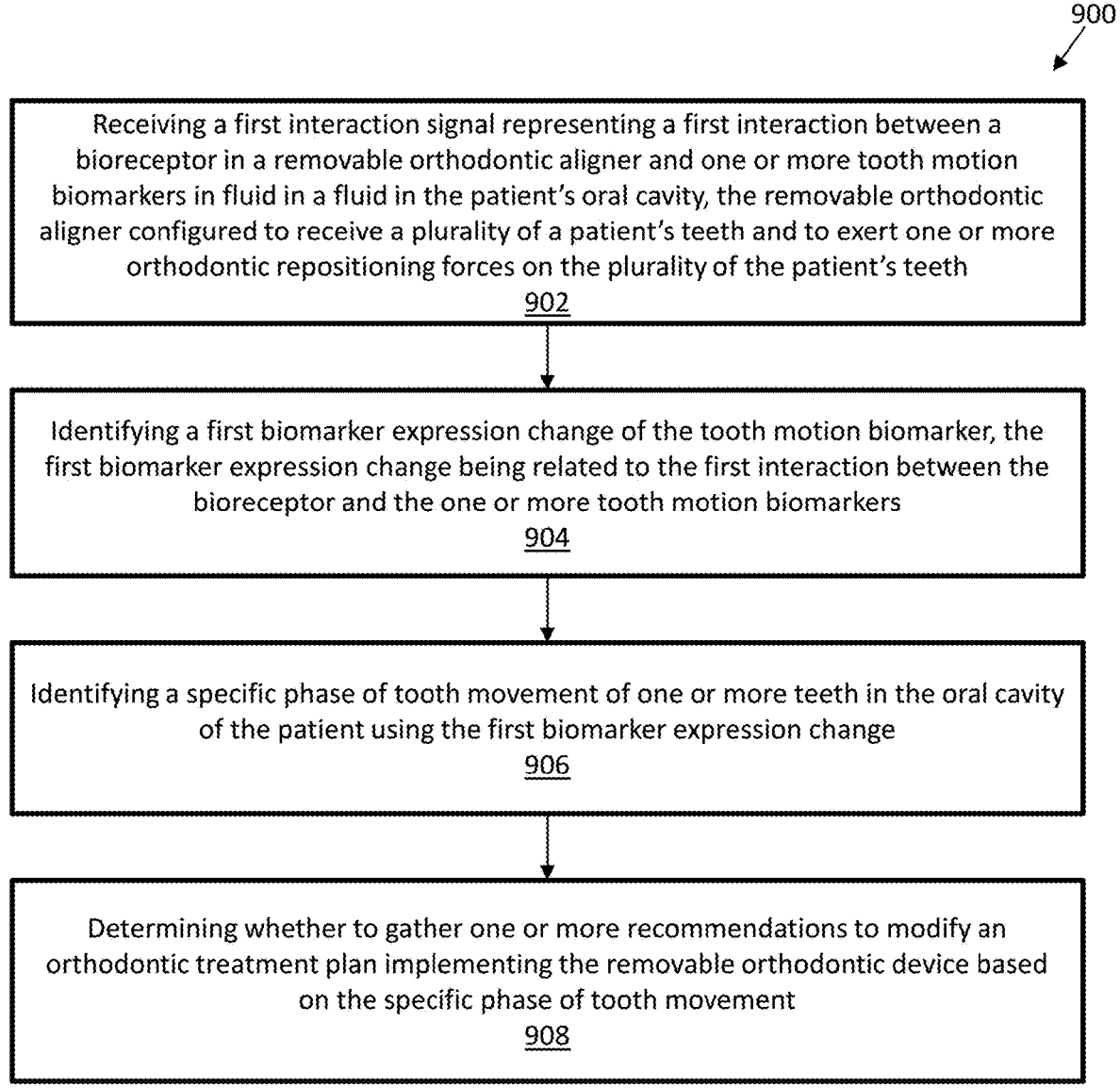
FIG. 9 illustrates an example of a method of modifying an orthodontic treatment plan using a removable orthodontic device including a biosensor.

FIG. 9 illustrates an example of a method of modifying an orthodontic treatment plan using a removable orthodontic device including a biosensor. In FIG. 9, the biosensor signal may be received by a processor on the removable orthodontic device and/or by a remote processor (e.g. a smartphone, computer, server, etc.). For example, the method may include receiving a first interaction signal representing a first interaction between the bioreceptor in a removable orthodontic aligner and one or more tooth motion biomarkers in fluid (e.g., saliva, GCF, blood, etc.) in a fluid in the patient's oral cavity, the removable orthodontic aligner configured to receive a plurality of a patient's teeth and to exert one or more orthodontic repositioning forces on the plurality of the patient's teeth 902. The interaction signal may be analog or digital, and may be stored and/or processed (filtered, amplified, etc.) including normalized to another biomarker signal, a control signal and/or a baseline.

The first biomarker expression change of the tooth motion biomarker may be identified 904. This first biomarker expression change may be related to the first interaction between the bioreceptor and the one or more tooth motion biomarkers. For example, one or more specific phase(s) of tooth movement of one or more teeth in the oral cavity of the patient may be identified using the first biomarker expression change 906.

The method may also include determining whether to gather one or more recommendations to modify an orthodontic treatment plan implementing the removable orthodontic device based on the specific phase of tooth movement 908. For example, a recommendation may be based on the level of the one or more biomarker signals, as described above. This recommendation may be derived from stored logic, and/or a memory (e.g., a look-up table, by machine learning, etc.).

Microfluidics

Any of the bio sensors described herein may include one or more microfluidics systems for capture, storage and analysis of intra-oral fluids, including chemical analysis. For example, any of these microfluidic systems may include hard or flexible/stretchable (such as silicone) materials with or without integrated electronics (including wireless communication electronics), and may be formed integrally with the apparatus (e.g., aligner) and/or be intimately and robustly bond to the surface of apparatus.

In some variations, the microfluidic system may include a network of reservoirs for embedded chemical agents that may respond in colorimetric fashion to biomarkers. The reservoirs may be connected by microfluidics channels. In some variations the microfluidics channels may be configured for active and/or passive metering, so that a fluid from within the patient's oral cavity (e.g., saliva and/or GCF) may be drawn into the microfluidics channel and passed into a sample chamber. The sample chamber may include, for example a colorometric indicator or other chemical agent that responds to one or more biomarkers in the fluid in a colorimetric manner. Alternatively, in some variations, the sample is processed in a microfluidics channel for later read-out (e.g., when removing the device from the mouth, and placing it into a separate storage and/or readout chamber.

In any of these variations, apparatus may include microfluidic channels that are configured to allow access to various sample and/or detection regions on the apparatus at various times. For example, the microfluidics device integrated into or on an aligner may be configured to provide timing via chrono-sampling of a fluid. For example, a microfluidic system can be designed to enable sampling with chronological order and controlled timing. In some variations, the timing of fluid within the microchannel may be timed actively, e.g., by the opening of a channel via release of a valve (e.g., an electromechanical valve, an electromagnetic value, a pressure valve, etc.). Examples of valves controlling fluid in a microfluidic network include piezoelectric, electrokinetics and chemical approaches. Capillary bursting valves (CBVs) are another variation of a valve for a microfluidic channel. CBVs block flows at pressures lower than their characteristic bursting pressures (BPs). When liquid in a single connected channel encounters two separate CBVs with different BPs, at sufficient pressures, the flow will proceed first through the valve with lower BP. In this way, locating two CBVs with different BPs near the intersection between two channels allows control of the direction of flow. The Young-Laplace equation gives the BP in a rectangular channel:

$$BP = -2\sigma\left[\frac{\cos\theta_1^*}{b} + \frac{\cos\theta_A}{h}\right] \quad [1]$$

where $\sigma$ is the surface tension of liquid, $\theta_A$ is the contact angle of the channel, $\theta_1^*$ is the $\min[\theta_A+\beta; 180°]$, $\beta$ is the diverging angle of the channel, b and h are the width and the height of the diverging section, respectively. For hydrophobic materials at high diverging angles, the BP increases with decreasing b and h.

Thus, by adjusting the angles and dimensions, the bursting pressure may be adjusted and in the context of a microfluidics channel, series of CBVs may be used to set up a sequence of timed regions that open as the fluid within the channel reaches the selected BP. For example, the diverging angles may be between 13° and 90°, or 13° and 120°. One of skill in the art would therefore be able to select the microfluidic channel lengths and BP configurations to arrange a series of microfluidics channels and chambers, which are valved by one or more control valves, including CBVs that open at predetermined time ranges to allow sampling over time.

In some variations the microfluidic channel may be opened by dissolving a material blocking the channel. The rate of dissolution may be calibrate to open the channel after a predetermined time period (e.g., minutes, hours, days, etc.). In some variations the dissolving material may include one or more reagents for use in detecting and/or storing the fluid in the microfluidics apparatus. For example, a blocking material may include a labeling material (e.g., such as an antibody, enzyme, substrate, etc.) for detection within a chamber blocked by the blocking material.

Figure 10A:
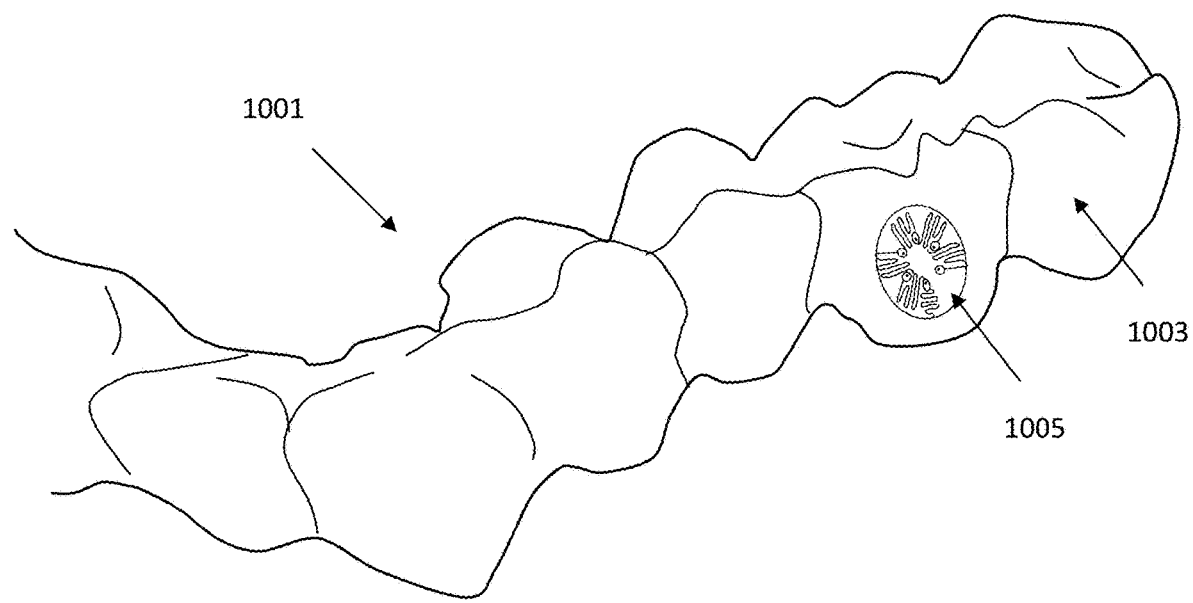
FIG. 10A is an example of an orthodontic apparatus (e.g., aligner) including a biosensor including microfluidics for assaying one or more biomarkers at different times.
Figure 10B:
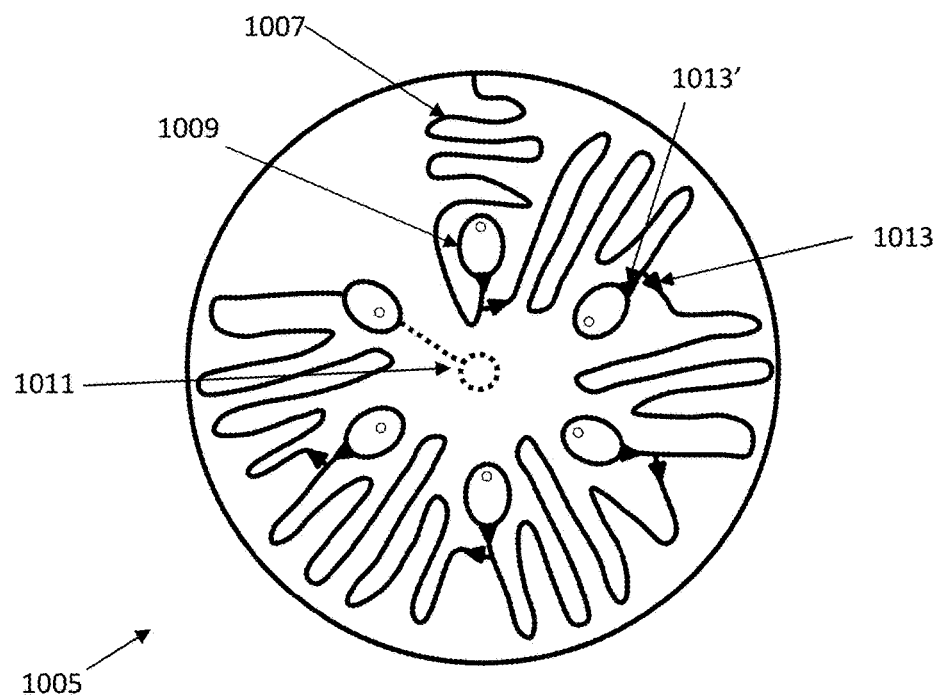
FIG. 10B is a schematic illustration of one example of a biosensor including microfluidics and assay chambers that may be operated in a chronological order to provide controlled sampling.

For example, FIGS. 10A-10H illustrate an example of an apparatus, configured as an aligner, that may be worn on a subject's teeth to provide sampling and/or storage of a fluid from the patient's oral cavity. In FIG. 10A, the aligner 1001 includes one or more tooth-receiving portions 1003 and is configured to be won over the patient's teeth. In this example, a microfluidics component 1005 may form part of a biosensor and may be included or incorporated into the aligner, as shown. FIG. 10B shows an enlarged view of the microfluidics portion of the exemplary apparatus. In this example, the microfluidics portion (e.g., of the biosensor) includes a plurality of microfluidics channels 1007 and chambers 1009 that are sequentially arranged within the device to "open" at different times; fluid (e.g., saliva, GCF) is drawn into the microfluidics portion at a metered rate toward each chamber. In addition, the lengths of microfluidics channels 1007 increases toward each chamber, requiring additional time for each channel to reach each chamber. The chambers are connected by microfluidics channels and the fluid may require a predetermined amount of time to reach each chamber. In some variations the chamber includes a portion of an assay (e.g. a colorimetric indicator) for detecting one or more biomarker. In FIG. 10B, each microfluidics chamber may also include a vent for preventing air bubbles or build-up in the channel(s); this vent may be a hydrophobic, air-permeable membrane that permits air to leave the microfluidics channel, but not allow additional saliva to pass into the channel/chamber. In the example shown in FIG. 10B, each channel into a chamber and from the chamber into the next length of channel (they are arranged in sequence) includes a valve 1013, 1013'. For example, the valve(s) may be CBVs as discussed above.

By staggering the timing of opening (access) through the microfluidic channels into the various chambers, the sampling and/or testing of the fluid from the oral cavity may be controlled. For example, the apparatus of FIGS. 10A-10B may be configured to sample fluid from the saliva every x hours (e.g., every 1 hour, every 2 hours, every 3 hours, ever 4 hours, every 6 hours, every 12 hours, every 24 hours, every 36 hours, every 48 hours, etc.). This is illustrated in FIGS. 10C-10H, showing staggered filling of sampling chamber 1021 at approximately 1 hour (FIG. 10C), 12 hours (FIG. 10D), 24 hours (FIG. 10E), 36 hours (FIG. 10F), 48 hours (FIG. 10G) and 60 hours (FIG. 10H); at each interval, an additional sampling/storage chamber is opened.

FIG. 11 is another example of a timed microfluidics sampling and/or testing region 1031. In this example, six microfluidic chambers 1039 are shown, each connected to a microfluidics channel 1034 that is metered by a separate valve 1032 that may be opened to allow fluid to flow into the microfluidics channel and into the chamber. The valve may be controlled actively or passively as mentioned above. In some variations the chambers include a preservative material and the material with the chambers 1039 may be held for later testing.

In some variations, one or more multiplexers may be used to sample and/or measure multiple biomarkers in controlled intervals. For example, a multiplexer may be used to provide access to one or more sample regions (chambers). The multiplexer and/or any active valves may be connected and controlled by control circuitry in the apparatus.

Variations

Also described herein are biosensors that are configured to use a biofuel as part of the biosensor. For example an electrochemical sensor may be formed using an enzyme that catalyzes a reaction in the presence of a biomarker to be identified; the reaction may be detected directly, e.g., when the enzymatic reaction results in an ionizing reaction and is coupled to an electrical conductor, or indirectly. For example, when using biofuel as biosensor, the biomarker may be detected, for example, by measuring how much voltage is generated in the biofuel. Enzymatic biofuels may work based on ionic current. For example, amperometric electrodes may be used to detect the level or presence of biomarkers, including ionic species, such as $O_2$, $H_2O_2$, NADH, $I_2$, etc. Similarly, ion-selective electrodes may be used (e.g., to detect pH, $NH_4$, $NH_3$, $CO_2$, $I^-$, $CN^{-1}$ etc. Any of these sensors may include a membrane (e.g., semi-permeable or selectively permeable membrane.

Other examples of biosensors may include paper-based bio sensors that may be integrated with an apparatus such as an aligner. The main constituent of paper is cellulose fiber, and this can be highly attractive for certain applications, as it allows liquid to penetrate within its hydrophilic fiber matrix without the need of an active pump or external source. Moreover, cellulose fibers can be functionalized, thus changing properties such as hydrophilicity, if desired, as well as its permeability and reactivity. The paper sensor may be at least partially enclosed by the aligner material, and may be directly exposed to the oral cavity or indirectly exposed (e.g., via a channel, including a microfluidics channel). The paper sensor may be formed of a fibrous material such as nitrocellulose, and may be patterned (e.g., via photolithography) or by printing including silk-screening-like processes. The biosensor may include a biomarker that is impregnated and/or applied and/or absorbed onto the paper into a detection pattern. Multiple positive/negative regions may be created. For example, a glucose-detecting region may use iodine, which may be enzymatically reduced in the presence of glucose, resulting in a detectable color change (e.g., from clear to brown). Thus, in general, any of the bio sensors described herein may be configured to be used with a cellulose (paper) substrate.

In general, as mentioned above, sampling of bio sensors can be conducted on an apparatus such as an aligner in an intraoral cavity and the biochemical or optical assays can be done in the aligner case. For instance, saliva or GCF sampling can be conducted using microfluidic system or paper-based system while the aligner is worn. When the aligner removed from the mouth and is placed in the case, optical assessment of the concentration of biomarkers in the sampled fluid can be done using a very small optical system integrated into the case. For example, the optical system may include one or more LEDs, and one or more photodiodes.

Any of the methods and apparatuses described herein may be used with one or more biosensors configured for lateral flow and/or vertical flow immunoassay for biomarker detection. Vertical flow immunoassays rely on the same basic principles as the more common lateral flow immunoassay format with some modifications. The most apparent difference between the two methods being the vertical and lateral flow of fluid. However, vertical flow technology may have advantages over traditional lateral flow assays, including reduced assay time (<5 minutes).

Vertical flow immunoassays can be used for rapid detection of an antigen(s) including biomarkers. Detection sensitivity may be in the lower nanogram per ml range even in complex sample matrices. For example, the biosensor may include an immobilized capture agent (e.g., antibody) on a reagent pad to which a sample such as saliva or GCF (with or without biomarker to be detected) is applied, e.g., via a microfluidics channel. Detection of the bound capture agent may be achieved through the binding of, for example, an antigen specific antibody conjugated to a detectable marker, such as a gold conjugate. This step completes a sandwich consisting of a capture agent (e.g., antibody), the biomarker (antigen) and finally the detectable marker (e.g., gold conjugate) and results in a direct and permanent visually detectable marker, such as a red dot indicating the presence of the biomarker. Alternative colors for detection may be achieved by using different types of detectable markers, such as nanoparticles conjugated to a probe for detection.

Biosensors integrated with aligners can be used for detection of biomarkers associated with oral and periodontal diseases such as, for example: DNA probes for detection of putative periodontal pathogens (e.g., *Porphyromonas gingivalis*, *Tanerella forsythensis*, *Treponema denticola*, *Actinobacillus actinomycetemcomitans*, etc.), host response factors (e.g., IL-1β; TNF-α; aspartate aminotransferase; elastase), connective tissue breakdown products (e.g., collagen telopeptides; osteocalcin; proteoglycans; fibronection fragments, etc.).

Any of the apparatuses including bio sensors and methods described herein may use aptamers. For example, any of these biosensors may be aptomer-based biosensors. Aptamers are single-stranded nucleic acids that selectively bind to target molecules. Aptamers may have high stability, resistance to denaturation and degradation, and may be easily modified.

EXAMPLES

A biosensor for use with an orthodontic device such as an aligner may include an enzyme or other protein-binding agent (e.g., antibody fragment, etc.) that is formed into a biosensor by a modified screen-printing electrode formation method. The apparatus may also include any of the electronics systems described herein, including a controller (e.g., microcontroller) and wireless communication sub-system, such as a Bluetooth (e.g., Bluetooth low energy, BLE) transceiver. The biosensor may be formed suing screen-printing technology onto a flexible substrate, such as PET (polyethylene terephthalate). The binding protein (e.g., enzyme) may be crosslinked to a reporter enzyme or indicator that, when the target protein is bound, activates the reporter so that this activity can be detected by the biotransducer. For example, in some instances the binding protein is an enzyme that engages with the target protein and has as a by-product a peroxide (e.g., $H_2O_2$); alternatively the binding protein may be modified such that it is conjugated to a peroxide-forming enzyme and when the target biomolecule is present (e.g., in a saliva sample), the enzyme is allowed to reach to form peroxide. In such cases, the bioreporter may include a material, such as Prussian-blue carbon, reacts with the byproduct to produce a current. For example, in biosensors in which peroxide is formed in the presence of the target biomarker, a current may therefore be detected as hydrogen peroxide contacts the bioreporter (e.g., Prussian Blue carbon). For example, the binding protein maybe fused with an enzyme (e.g., peroxidase); in the presence of the biomarker to which the binding protein binds, the enzyme is free to convert substrate (preferably the biomarker) into an oxidized or reduced form to generate an electrical current on the biosensor, particularly compared to the reference/control electrode, which may not include the binding protein.

In one example, a conductive ink may be printed onto a substrate (e.g., an Ag/AgCl conductive ink) to form the base of an electrode, contact pad/region and one or more traces. A reference electrode as well as a biosensor electrode may be formed; the biosensor may act as an electrochemical sensor. Interaction and/or binding of the biomarker protein to the bioreceptor may be detected either directly by the bioreporter (e.g., as it produces an oxidation or reduction of the bioreporter) or indirectly. Thus, both active (biosensor) and control electrodes may include the bioreporter (e.g., graphite ink such as Prussian-blue graphite ink in variations in which a peroxide is formed by the interaction with the biomarker). The bioreporter may also be printed onto the working (biosensor) and counter electrodes. An insulator layer (e.g., of dielectric material) may also be used. In some variations a sacrificial layer of material that is consumed by or consumable by the bioreceptor and/or bioreporter when interacting with the biomarker may also be used. After each printing step, the printed layers may be allowed to cure (e.g., at room temperature or greater). Any appropriate size electrode (working and counter electrodes) may be used, for example, 0.5 mm diameter, 1 mm diameter, 2 mm diameter, 3 mm diameter, 4 mm diameter, etc. The biosensor may then be modified to include the protein that interacts with the biosensor, such as an enzyme, antibody fragment, etc., and an antibiofoulding coating and/or membrane may be used (e.g., electropolymerized o-phenylenediamine (PPD).

Thus, a biosensor as described herein may be printed by, e.g., a screening technique in which a substrate (which may be the aligner) is secured and a conductive layer (e.g., Ag/AgCl-based ink) is firstly applied to define the conductive underlayer of the biosensor as well as a reference electrode; the conductive layer may be patterned directly onto the substrate. Next, a catalytic layer may be applied. For example, a carbon or metal-based ink containing any associated catalytic or biocatalytic functionality may be applied onto the conductor to define the working and counter electrode. Thereafter, an insulator may be applied on the conductor and catalytic layers to insulate all but the contact pads and the upper portion of the electrodes. Subsequent to each printing routine, the sensor may be annealed in a temperature-controlled oven at an appropriate temperature to evaporate and volatile solvents. Thereafter, electrochemical activation of the active material may be performed via repetitive cyclic voltammograms or extended duration amperometry. Cyclic voltammetry may also be executed in a sulfuric acid solution of moderate strength in order to electrochemically clean the electrode surface and attenuate any impurities that may interfere with measurements. Electrochemical deposition of conducting polymers (i.e. poly (pyrrole), poly(aniline)) or plating of metal catalysts (i.e. palladium, platinum, gold) may also be executed to functionalize/prepare the electrode surface for enhanced detection. Dry reagents, electroactive mediators, and/or permselective membranes may then be dispensed on the surface to achieve pH adjustment, reduce the overpotential required to excite the electroactive analyte of interest, and/or reject potential interfering compounds. Alternatively, rather than screening, these layers may be applied by stamping.

FIGS. 7A-7C illustrate another example of a bio sensor that may be included as part of a dental apparatus. In this example the biosensor detects a change in pressure due to swelling of a material that increases and/or decreases volume with binding to a biomarker. For example a sensor may be made based on binding of the biomarker to the gel, which may change the ionic conductivity of the gel, resulting in swelling. The swelling of the gel may be detected mechanically (e.g., by a force sensor), electrictromechanically (e.g., using a microcantilever) and/or optically (e.g., using an optical fiber). In one example, a glucose sensor may be formed by including a glucose-binding agent (e.g., phenylboronic acid) attached to a gel. A change in ionic conductivity of the gel may be measured as the binding reaction changes the swelling of the gel.

In some variations the gel may be coated to a force sensor (e.g., a gel-coated silicon microcantilever) to and the force sensor may be used to detect swelling in response to changes in the biomarker species. For example, a pH sensors may be formed using a gel that swells/contracts based on pH. In addition, a sensor to detect enzymatic reactions (enzyme activity) may be formed by tethering an enzymatic target (or the enzyme itself) to a hydrogel. Enzymatic activity may result induce swelling, which may be detected. In some variations, swelling may be caused by an ionic concentration (e.g., Calcium concentration). A crosslinked polyacrylic acid gel, which can undergo single-chain aggregation in the presence of $Ca^{2+}$ may be used to detect local calcium concentration by swelling/shrinking based on the concentration of calcium.

FIG. 7A shows an example of a dental appliance, configured as an aligner 704 including a biosensor 700. This biosensor may be permanently or removably mounted to the outside and/or inside of the appliance by a mount 715. A schematic of the bio sensor is shown in FIGS. 7B and 7C. The biosensor may include a sample port 703 exposing a swellable hydrogel 705 that is configured to change volume (e.g., swell) when exposed to one or more particular biomarker. The change in volume may be detected by the control circuitry 709 within the biosensor. For example the control circuitry may include a force sensor that determines the force due to swelling, and/or by electrical changes (e.g., changes in conductivity/resistivity) due to binding and/or activity of the target biomolecule. The control circuitry may also include any of the other components described above (e.g., one or more processors, memories, power regulator circuitry, wireless communication circuitry, etc. FIG. 7B shows the biosensor prior to swelling and FIG. 7C shows the biosensor after/during swelling.

Customizing Patient Treatment Using Biomarker Data

In any of the methods and apparatuses described herein, one or more biomarkers may be monitored and the data from monitoring the biomarker may be used to modify an orthodontic treatment plan. Monitoring may be continuous, e.g., using a dental appliance that includes one or more sensors within the patient's oral cavity, as described above, or it may be performed by sampling from the oral cavity and processing the sample outside of the oral cavity.

The dental treatment may be modified base on the absence or presence of a maker and/or the level (e.g., a normalized level) of one or more markers. For example, a patient-specific orthodontic treatment plan may be modified based on a biomarker detected during a treatment stage. In one variation a marker for one or more of inflammation (e.g., acute inflammation, such as cytokines and/or prostaglandins) and/or bone remodeling (e.g., Glycosaminoglycans) may be detected following an initial first or second treatment stage. In some variations, one or more initial measurements, e.g., baseline, may be used specific to a patient and compared to later measurements to detect a change. If the change in level of one or more biomarkers is below a minimum threshold (e.g., no change, change below about x %, where x is 5%, 10%, 15%, 20%, 25%, 30%, 35%, 40%, 50%, 60%, 70%, 80%, 90%, etc. compared to a baseline and/or standard value), then the orthodontic treatment plan may be modified to increase the amount of movement during the next stage. If the change in level of one or more biomarkers is above a maximum threshold (e.g., change of greater than y %, where y is 30%, 40%, 50%, 60%, 70%, 80%, 90%, 100%, 110%, 120%, 130%, 140%, 150%, 160%, 170%, 180%, 190% 200%, etc.) then the orthodontic treatment plan may be modified to decrease the relative tooth movement during the next stage and/or the duration of the current stage.

Alternatively, or additionally, the biomarkers level(s) may be used to adjust the duration that one or more dental appliances (e.g., aligners) in a series of progressive dental appliances are worn. For example, if the one or more biomarkers consistent with an acute stage of tooth movement remain elevated during a treatment stage, the duration of that stage may be extended.

Thus, a series or sequence of dental appliances may be modified based on the level(s) of one or more biomarkers, including modifying the dental appliances (e.g., adjusting tooth movement at each stage of the series or sequence) and/or adjusting the duration that the one or more appliances is worn (e.g., wearing them for longer or shorter time periods), and/or wearing them for a lesser or greater part of the day. In some variations, the duration of that a final appliance (e.g., a retainer) is to be worn may be determined at least in part by monitoring one or more biomarkers, such as markers of bone remodeling, markers for inflammation, etc. For example, a retainer may be worn until one or more biomarkers returns to within some predetermined range of a baseline and/or standard value. For example, a patient may continue to wear a retainer until the levels of one or more biomarkers (e.g., Calgranulin-B, Serum albumin precursor, Immunoglobulin J chain, Ig alpha-1 chain C region, Cysteine-rich secretory protein 3 precursor (CRISP-3), Hemoglobin subunit beta, Stratifin, and soluble RANK Ligand (sRANKL), prostaglandin E2, Substance P, epidermal growth factor, transforming growth factor, Receptor activator of nuclear factor kappa-B ligand (RANKL), Granulocyet macrophage colony stimulation factor, α2 microglobulin, Interleukin 1β, Myeloperoxidase, hyaluronic acid and/or Chondroitin sulfate, etc.) is within a predetermined range of the baseline and/or standard value (e.g., within about 5%, 10%, 15%, 20%, 25%, 30%, 35%, 40%, 50%, etc. of the baseline and/or a standard value).

As discussed above, in some variations, an orthodontic treatment plan may be modified or customized based on biosensor data. For example, a series of aligners may include one or more aligners with one or more sensor for detecting a biomarker while wearing the apparatus. One or more sensors may record data.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
    monitoring a performance of an orthodontic device for a dentition within an oral cavity of a patient, the orthodontic device including:
        a plurality of tooth receiving cavities configured to receive and exert one or more orthodontic repositioning forces on a plurality of teeth of the dentition; and
        at least one biosensor system comprising at least one first bioreceptor configured to interact with one or more tooth motion biomarkers in a fluid in the oral cavity of the patient, the one or more tooth motion biomarkers associated with movement of the plurality of teeth in response to the one or more orthodontic repositioning forces, the at least one biosensor system further comprising at least one second bioreceptor configured to interact with one or more compliance biomarkers in the fluid in the oral cavity of the patient, the one or more compliance biomarkers associated with compliance of the patient to a treatment plan;
    wherein monitoring the performance comprises:
        monitoring a first interaction signal using the at least one biosensor system, the first interaction signal associated with a first interaction between the at least one first bioreceptor and the one or more tooth motion biomarkers;
        comparing first signal attributes of the first interaction signal against a first threshold for a specific phase of tooth movement;
        monitoring a second interaction signal associated with a second interaction between the at least one second bioreceptor and the one or more compliance biomarkers;
        comparing second signal attributes of the second interaction signal against a second threshold for a specific measure of compliance for the patient; and
        providing one or more recommendations for changing the treatment plan based on the comparing of the first interaction signal attributes against the first threshold and the comparing of the second signal attributes against the second threshold.

2. The method of claim 1, wherein the first signal attributes comprise a signal strength of the first interaction signal.

3. The method of claim 1, wherein the one or more recommendations for changing the treatment plan comprise one or more recommendations to change an orthodontic appliance based on the specific measure of compliance for the patient.

4. The method of claim 1, wherein the one or more recommendations for changing the treatment plan comprises one or more recommendations to change an orthodontic appliance at a specified time.

5. The method of claim 1, wherein:
the specific phase of tooth movement corresponds to a velocity of root movement of roots of the plurality of teeth; and
the method further comprises determining when the velocity of root movement is substantially zero, thereby indicating a conclusion of at least a portion of the treatment plan.

6. The method of claim 1, further comprising communicating data related to the one or more recommendations to a remote device.

7. The method of claim 6, wherein the remote device is one or more of a smart phone and a dedicated receiver.

8. The method of claim 1, wherein the one or more tooth motion biomarkers are monitored over a predetermined time.

9. The method of claim 1, wherein the first interaction signal is sent by the at least one biosensor system at predetermined intervals of time.

10. The method of claim 1, further comprising determining a rate of tooth movement based on the first interaction signal.

11. The method of claim 1, wherein the one or more tooth motion biomarkers is one or more of: Calgranulin-B, Serum albumin precursor, Immunoglobulin J chain, Ig alpha-1 chain C region, Cysteine-rich secretory protein 3 precursor (CRISP-3), Hemoglobin subunit beta, Stratifin, and soluble RANK Ligand (sRANKL).

12. The method of claim 1, wherein the at least one first bioreceptor comprises an enzyme that selectively acts on the one or more tooth motion biomarkers.

13. The method of claim 1, wherein the fluid comprises saliva or gingival crevicular fluid (GCF).

14. A method comprising:
monitoring a performance of a plurality of orthodontic devices for a dentition within an oral cavity of a patient, the plurality of orthodontic devices implementing a plurality of stages of a treatment plan, wherein:
a first orthodontic device of the plurality of orthodontic devices includes:
a plurality of first tooth receiving cavities configured to receive and exert one or more first orthodontic repositioning forces on a plurality of teeth of the dentition; and
a first biosensor system comprising at least one first bioreceptor configured to interact with one or more tooth motion biomarkers in a fluid in the oral cavity of the patient, the one or more tooth motion biomarkers associated with movement of the plurality of teeth in response to the one or more first orthodontic repositioning forces;
a second orthodontic device of the plurality of orthodontic devices includes:
a plurality of second tooth receiving cavities configured to receive and exert one or more second orthodontic repositioning forces on the plurality of teeth of the dentition; and
a second biosensor system comprising at least one second bioreceptor configured to interact with one or more compliance biomarkers in the fluid in the oral cavity of the patient, the one or more compliance biomarkers associated with compliance of the patient to the treatment plan;
wherein monitoring the performance comprises:
monitoring a first interaction signal using the first biosensor system, the first interaction signal associated with a first interaction between the at least one first bioreceptor and the one or more tooth motion biomarkers;
monitoring a second interaction signal using the second biosensor system, the second interaction signal associated with a second interaction between the at least one second bioreceptor and the one or more compliance biomarkers;
evaluating first signal attributes of the first interaction signal against a first threshold for a specific phase of tooth movement;
evaluating second signal attributes of the second interaction signal against a second threshold for specific measure of compliance for the patient; and
providing one or more recommendations for changing the treatment plan based on the evaluation of the first signal attributes against the first threshold and the evaluation of the second signal attributes against the second threshold.

15. The method of claim 14, wherein the first signal attributes comprise a signal strength of the first interaction signal.

16. The method of claim 14, wherein the one or more recommendations for changing the treatment plan comprise one or more recommendations to change an orthodontic appliance based on the specific measure of compliance for the patient.

17. The method of claim 14, wherein:
the specific phase of tooth movement corresponds to a velocity of root movement of roots of the plurality of teeth; and
the method further comprises determining when the velocity of root movement is substantially zero, thereby indicating a conclusion of at least a portion of the treatment plan.

18. The method of claim 14, wherein the at least one first bioreceptor comprises an enzyme that selectively acts on the one or more tooth motion biomarkers.

19. The method of claim 14, wherein the one or more tooth motion biomarkers is one or more of: Calgranulin-B, Serum albumin precursor, Immunoglobulin J chain, Ig alpha-1 chain C region, Cysteine-rich secretory protein 3 precursor (CRISP-3), Hemoglobin subunit beta, Stratifin, and soluble RANK Ligand (sRANKL).

* * * * *